US006500926B1

(12) United States Patent
Birkenbach et al.

(10) Patent No.: US 6,500,926 B1
(45) Date of Patent: Dec. 31, 2002

(54) EPSTEIN BARR VIRUS INDUCED GENES

(75) Inventors: Mark Birkenbach, Tinley Park, IL (US); Elliot Kieff, Brookline, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/536,954

(22) Filed: Mar. 28, 2000

Related U.S. Application Data

(62) Division of application No. 08/352,678, filed on Nov. 30, 1994, now Pat. No. 6,043,351, which is a continuation of application No. 07/980,518, filed on Nov. 25, 1992, now abandoned.

(51) Int. Cl.$^7$ .......................... C07H 21/04; C07K 14/00
(52) U.S. Cl. ............................ 530/350; 435/5; 530/350
(58) Field of Search .......................... 435/5; 536/24.32; 530/350, 300

(56) References Cited

U.S. PATENT DOCUMENTS

| | | | | |
|---|---|---|---|---|
| 5,262,529 A | * | 11/1993 | Dryja et al. | 536/24.31 |
| 5,744,301 A | * | 4/1998 | Birkenbach et al. | 435/6 |
| 5,753,516 A | * | 5/1998 | Heagy et al. | 436/501 |
| 5,759,804 A | * | 6/1998 | Godiska et al. | 435/69.1 |
| 6,043,351 A | * | 3/2000 | Birkenbach et al. | 536/23.72 |

FOREIGN PATENT DOCUMENTS

| | | | | |
|---|---|---|---|---|
| WO | WO 90/05147 | * | 5/1990 | C07K/15/06 |

OTHER PUBLICATIONS

Wang et al., Proc. Natl. Acad. Sci., 84:3452.*
Alfieri et al., *Virology* 181:595–608 (1991).
Bayliss and Wolf, *J. gen. Virol.* 56:105–118 (1981).
Bayliss et al., *J. of Virol. Methods* 7:229–239 (1983).
Birkenbach et al., *J. of Virology* 63(9):4079–4084 (1989).
Calender et al., *Proc. Natl. Acad. Sciences USA* 84:8060–8064 (1987).
Favrot et al., *Int. J. of Cancer* 38:901–906 (1986).
Ehlin–Henriksson et al., *Int. J. of Cancer* 39:211–218 (1987).
Gregory et al., *J. of General Virology* 71:1481–1495 (1990).
Henderson et al., *Cell* 65:1107–1115 (1991).
Hummel and Kieff, *Proc. Natl. Acad. Sci. USA* 79:5698–5702 (Sep. 1982).
Knutson, J.C., *J. of Virology* 64(6):2530–2536 (1990).
Qualtiere and Pearson, *Int. J. Cancer* 23:808–817 (1979).
Rowe et al., *Int. J. of Cancer* 37:367–373 (1986).
Rowe et al., *EMBO Journal* 6(9):2743–2751 (1987).
Spira et al., *J. of Immunology* 126(1):122–126 (1981).
Thorley–Lawson et al., *J. of Immunology* 134(5): 3007–3012 (1985).
Wang et al., *J. of Virology* 64(5)2309–2318 (1990).
Wang et al., *Proc. Natl. Acad. Sciences USA* 84:3452–3456 (1987).
Wang et al., *J. of Virology* 64(7):3407–3416 (1990).
GenBank Acc. No. T02587, May 26, 1992.
Stratagene Catalog, 1998 p. 39.

* cited by examiner

*Primary Examiner*—W. Gary Jones
*Assistant Examiner*—Jeanine Goldberg
(74) *Attorney, Agent, or Firm*—Wolf, Greenfield & Sacks, P.C.

(57) ABSTRACT

The present invention relates, in general, to Epstein Barr virus induced (EBI) genes. In particular, the present invention relates to DNA segments coding for EBI 1, EBI 2, or EBI 3 polypeptides; EBI 1, EBI 2, or EBI 3 polypeptides; recombinant DNA molecules; cells containing the recombinant DNA molecules; antisense EBI 1, EBI 2, or EBI 3 constructs; antibodies having binding affinity to an EBI 1, EBI 2, or EBI 3 polypeptide; hybridomas containing the antibodies; nucleic acid probes for the detection of the presence of Epstein Barr Virus; a method of detecting Epstein Barr virus in a sample; and kits containing nucleic acid probes or antibodies.

30 Claims, 17 Drawing Sheets

```
GGAATTCCGT AGTGCGAGGC CGGGCACAGC CTTCCTGTGT GGTTTTACCG CCCAGAGAGC      60
         * **
GTC ATG GAC CTG GGG AAA CCA ATG AAA AGC GTG CTG GTG GTG GCT CTC      108
    Met Asp Leu Gly Lys Pro Met Lys Ser Val Leu Val Val Ala Leu
    1           5                  10                 15

CTT GTC ATT TTC CAG GTA TGC CTG TGT CAA GAT GAG GTC ACG GAC GAT      156
Leu Val Ile Phe Gln Val Cys Leu Cys Gln Asp Glu Val Thr Asp Asp
            20                  25                  30

TAC ATC GGA GAC AAC ACC ACA GTG GAC TAC ACT TTG TTC GAG TCT TTG      204
Tyr Ile Gly Asp Asn Thr Thr Val Asp Tyr Thr Leu Phe Glu Ser Leu
            35 CHO ### ###     40                  45

TGC TCC AAG AAG GAC GTG CGG AAC TTT AAA GCC TGG TTC CTC CCT ATC      252
Cys Ser Lys Lys Asp Val Arg Asn Phe Lys Ala Trp Phe Leu Pro Ile
            50                  55                  60

ATG TAC TCC ATC ATT TGT TTC GTG GGC CTA CTG GGC AAT GGG CTG GTC      300
Met Tyr Ser Ile Ile Cys Phe Val Gly Leu Leu Gly Asn Gly Leu Val
            65                  70                  75

GTG TTG ACC TAT ATC TAT TTC AAG AGG CTC AAG ACC ATG ACC GAT ACC      348
Val Leu Thr Tyr Ile Tyr Phe Lys Arg Leu Lys Thr Met Thr Asp Thr
        80              85                  90                  95

TAC CTG CTC AAC CTG GCG GTG GCA GAC ATC CTC TTC CTC CTG ACC CTT      396
Tyr Leu Leu Asn Leu Ala Val Ala Asp Ile Leu Phe Leu Leu Thr Leu
                    100                 105                 110

CCC TTC TGG GCC TAC AGC GCG GCC AAG TCC TGG GTC TTC GGT GTC CAC      444
Pro Phe Trp Ala Tyr Ser Ala Ala Lys Ser Trp Val Phe Gly Val His
                115                 120                 125

TTT TGC AAG CTC ATC TTT GCC ATC TAC AAG ATG AGC TTC TTC AGT GGC      492
Phe Cys Lys Leu Ile Phe Ala Ile Tyr Lys Met Ser Phe Phe Ser Gly
            130                 135                 140

ATG CTC CTA CTT CTT TGC ATC AGC ATT GAC CGC TAC GTG GCC ATC GTC      540
Met Leu Leu Leu Leu Cys Ile Ser Ile Asp Arg Tyr Val Ala Ile Val
            145                 150                 155
```

FIG.1A-1

```
CAG GCT GTC TCA GCT CAC CGC CAC CGT GCC CGC GTC CTT CTC ATC AGC        588
Gln Ala Val Ser Ala His Arg His Arg Ala Arg Val Leu Leu Ile Ser
160             165             170             175

AAG CTG TCC TGT GTG GGC AGC GCC ATA CTA GCC ACA GTG CTC TCC ATC        636
Lys Leu Ser Cys Val Gly Ser Ala Ile Leu Ala Thr Val Leu Ser Ile
                180             185             190

CCA GAG CTC CTG TAC AGT GAC CTC CAG AGG AGC AGC AGT GAG CAA GCG        684
Pro Glu Leu Leu Tyr Ser Asp Leu Gln Arg Ser Ser Ser Glu Gln Ala
            195             200             205

ATG CGA TGC TCT CTC ATC ACA GAG CAT GTG GAG GCC TTT ATC ACC ATC        732
Met Arg Cys Ser Leu Ile Thr Glu His Val Glu Ala Phe Ile Thr Ile
        210             215             220

CAG GTG GCC CAG ATG GTG ATC GGC TTT CTG GTC CCC CTG CTG GCC ATG        780
Gln Val Ala Gln Met Val Ile Gly Phe Leu Val Pro Leu Leu Ala Met
    225             230             235

AGC TTC TGT TAC CTT GTC ATC ATC CGC ACC CTG CTC CAG GCA CGC AAC        828
Ser Phe Cys Tyr Leu Val Ile Ile Arg Thr Leu Leu Gln Ala Arg Asn
240             245             250             255

TTT GAG CGC AAC AAG GCC ATC AAG GTG ATC ATC GCT GTG GTC GTG GTC        876
Phe Glu Arg Asn Lys Ala Ile Lys Val Ile Ile Ala Val Val Val Val
                260             265             270

TTC ATA GTC TTC CAG CTG CCC TAC AAT GGG GTG GTC CTG GCC CAG ACG        924
Phe Ile Val Phe Gln Leu Pro Tyr Asn Gly Val Val Leu Ala Gln Thr
            275             280             285

GTG GCC AAC TTC AAC ATC ACC AGT AGC ACC TGT GAG CTC AGT AAG CAA        972
Val Ala Asn Phe Asn Ile Thr Ser Ser Thr Cys Glu Leu Ser Lys Gln
        290     CHO ### ### 295             300

CTC AAC ATC GCC TAC GAC GTC ACC TAC AGC CTG GCC TGC GTC CGC TGC       1020
Leu Asn Ile Ala Tyr Asp Val Thr Tyr Ser Leu Ala Cys Val Arg Cys
    305             310             315
```

FIG.1A-2

| | |
|---|---|
| TGC GTC AAC CCT TTC TTG TAC GCC TTC ATC GGC GTC AAG TTC CGC AAC<br>Cys Val Asn Pro Phe Leu Tyr Ala Phe Ile Gly Val Lys Phe Arg Asn<br>320            325            330            335 | 1068 |
| GAT ATC TTC AAG CTC TTC AAG GAC CTG GGC TGC CTC AGC CAG GAG CAG<br>Asp Ile Phe Lys Leu Phe Lys Asp Leu Gly Cys Leu Ser Gln Glu Gln<br>340            345            350 | 1116 |
| CTC CGG CAG TGG TCT TCC TGT CGG CAC ATC CGG CGC TCC TCC ATG AGT<br>Leu Arg Gln Trp Ser Ser Cys Arg His Ile Arg Arg Ser Ser Met Ser<br>355            360            365 | 1164 |
| GTG GAG GCC GAG ACC ACC ACC ACC TTC TCC CCA TAGGCGACTC TTCTGCCTGG<br>Val Glu Ala Glu Thr Thr Thr Thr Phe Ser Pro ***<br>370            375 | 1217 |
| ACTAGAGGGA CCTCTCCCAG GGTCCCTGGG GTGGGGATAG GGAGCAGATG CAATGACTCA | 1277 |
| GGACATCCCC CCGCCAAAAG CTGCTCAGGG GAAAAAGCAG CTCTCCCCTC AGAGTGCAAG | 1337 |
| CCCCTGCTCC AGAAGATAGC TTCACCCCAA TCCCAGCTAC CTCAACCAAT GCCAAAAAAA | 1397 |
| GACAGGGCTG ATAAGCTAAC ACCAGACAGA CAACACTGGG AAACAGAGGC TATTGTCCCC | 1457 |
| TAAACCAAAA ACTGAAAGTG AAAGTCCAGA AACTGTTCCC ACCTGCTGGA GTGAAGGGGC | 1517 |
| CAAGGAGGGT GAGTGCAAGG GGCGTGGGAG TGGCCTGAAG AGTCCTCTGA ATGAACCTTC | 1577 |
| TGGCCTCCCA CAGACTCAAA TGCTCAGACC AGCTCTTCCG AAAACCAGGC CTTATCTCCA | 1637 |
| AGACCAGAGA TAGTGGGGAG ACTTCTTGGC TTGGTGAGGA AAAGCGGACA TCAGCTGGTC | 1697 |
| AAACAAACTC TCTGAACCCC TCCCTCCATC GTTTTCTTCA CTGTCCTCCA AGCCAGCGGG | 1757 |
| AATGGCAGCT GCCACGCCGC CCTAAAAGCA CACTCATCCC CTCACTTGCC GCGTCGCCCT | 1817 |
| CCCAGGCTCT CAACAGGGGA GAGTGTGGTG TTTCCTGCAG GCCAGGCCAG CTGCCTCCGC | 1877 |
| GTGATCAAAG CCACACTCTG GGCTCCAGAG TGGGGATGAC ATGCACTCAG CTCTTGGCTC | 1937 |

FIG.1A-3

```
CACTGGGATG GGAGGAGAGG ACAAGGGAAA TGTCAGGGGC GGGGAGGGTG ACAGTGGCCG    1997

CCCAAGGCCA CGAGCTTGTT CTTTGTTCTT TGTCACAGGG ACTGAAAACC TCTCCTCATG    2057

TTCTGCTTTC GATTCGTTAA GAGAGCAACA TTTTACCCAC ACACAGATAA AGTTTTCCCT    2117

TGAGGAAACA ACAGCTTTAA AAAAAAAAAA GGAATTC                              2154
```

FIG.1A-4

```
GGAATTCCCT GATATACACC TGGACCACCA CCA ATG GAT ATA CAA ATG GCA AAC  54
            * **                        Met Asp Ile Gln Met Ala Asn
                                         1               5

AAT TTT ACT CCG CCC TCT GCA ACT CCT CAG GGA AAT GAC TGT GAC CTC  102
Asn Phe Thr Pro Pro Ser Ala Thr Pro Gln Gly Asn Asp Cys Asp Leu
CHO ### ###
         10              15              20

TAT GCA CAT CAC AGC ACG GCC AGG ATA GTA ATG CCT CTG CAT TAC AGC  150
Tyr Ala His His Ser Thr Ala Arg Ile Val Met Pro Leu His Tyr Ser
         25              30              35

CTC GTC TTC ATC ATT GGG CTC GTG GGA AAC TTA CTA GCC TTG GTC GTC  198
Leu Val Phe Ile Ile Gly Leu Val Gly Asn Leu Leu Ala Leu Val Val
         40              45              50              55

ATT GTT CAA AAC AGG AAA AAA ATC AAC TCT ACC ACC CTC TAT TCA ACA  246
Ile Val Gln Asn Arg Lys Lys Ile Asn Ser Thr Thr Leu Tyr Ser Thr
                  60              65              70

AAT TTG GTG ATT TCT GAT ATA CTT TTT ACC ACG GCT TTG CCT ACA CGA  294
Asn Leu Val Ile Ser Asp Ile Leu Phe Thr Thr Ala Leu Pro Thr Arg
              75              80              85

ATA GCC TAC TAT GCA ATG GGC TTT GAC TGG AGA ATC GGA GAT GCC TTG  342
Ile Ala Tyr Tyr Ala Met Gly Phe Asp Trp Arg Ile Gly Asp Ala Leu
              90              95             100

TGT AGG ATA ACT GCG CTA GTG TTT TAC ATC AAC ACA TAT GCA GGT GTG  390
Cys Arg Ile Thr Ala Leu Val Phe Tyr Ile Asn Thr Tyr Ala Gly Val
       105             110             115
```

FIG.1B-1

```
AAC TTT ATG ACC TGC CTG AGT ATT GAC CGC TTC ATT GCT GTG GTG CAC  438
Asn Phe Met Thr Cys Leu Ser Ile Asp Arg Phe Ile Ala Val Val His
120             125             130             135

CCT CTA CGC TAC AAC AAG ATA AAA AGG ATT GAA CAT GCA AAA GGC GTG  486
Pro Leu Arg Tyr Asn Lys Ile Lys Arg Ile Glu His Ala Lys Gly Val
                140             145             150

TGC ATA TTT GTC TGG ATT CTA GTA TTT GCT CAG ACA CTC CCA CTC CTC  534
Cys Ile Phe Val Trp Ile Leu Val Phe Ala Gln Thr Leu Pro Leu Leu
                155             160             165

ATC AAC CCT ATG TCA AAG CAG GAG GCT GAA AGG ATT ACA TGC ATG GAG  582
Ile Asn Pro Met Ser Lys Gln Glu Ala Glu Arg Ile Thr Cys Met Glu
                170             175             180

TAT CCA AAC TTT GAA GAA ACT AAA TCT CTT CCC TGG ATT CTG CTT GGG  630
Tyr Pro Asn Phe Glu Glu Thr Lys Ser Leu Pro Trp Ile Leu Leu Gly
                185             190             195

GCA TGT TTC ATA GGA TAT GTA CTT CCA CTT ATA ATC ATT CTC ATC TGC  678
Ala Cys Phe Ile Gly Tyr Val Leu Pro Leu Ile Ile Ile Leu Ile Cys
200             205             210             215

TAT TCT CAG ATC TGC TGC AAA CTC TTC AGA ACT GCC AAA CAA AAC CCA  726
Tyr Ser Gln Ile Cys Cys Lys Leu Phe Arg Thr Ala Lys Gln Asn Pro
                220             225             230

CTC ACT GAG AAA TCT GGT GTA AAC AAA AAG GCT CTC AAC ACA ATT ATT  774
Leu Thr Glu Lys Ser Gly Val Asn Lys Lys Ala Leu Asn Thr Ile Ile
                235             240             245

CTT ATT ATT GTT GTC TTT GTT CTC TGT TTC ACA CCT TAC CAT GTT GCA  822
Leu Ile Ile Val Val Phe Val Leu Cys Phe Thr Pro Tyr His Val Ala
                250             255             260
```

FIG.1B-2

```
ATT ATT CAA CAT ATG ATT AAG AAG CTT CGT TTC TCT AAT TTC CTG GAA    870
Ile Ile Gln His Met Ile Lys Lys Leu Arg Phe Ser Asn Phe Leu Glu
    265             270             275

TGT AGC CAA AGA CAT TCG TTC CAG ATT TCT CTG CAC TTT ACA GTA TGC    918
Cys Ser Gln Arg His Ser Phe Gln Ile Ser Leu His Phe Thr Val Cys
280             285             290             295

CTG ATG AAC TTC AAT TGC TGC ATG GAC CCT TTT ATC TAC TTC TTT GCA    966
Leu Met Asn Phe Asn Cys Cys Met Asp Pro Phe Ile Tyr Phe Phe Ala
            300             305             310

TGT AAA GGG TAT AAG AGA AAG GTT ATG AGG ATG CTG AAA CGG CAA GTC    1014
Cys Lys Gly Tyr Lys Arg Lys Val Met Arg Met Leu Lys Arg Gln Val
            315             320             325

AGT GTA TCG ATT TCT AGT GCT GTG AAG TCA GCC CCT GAA GAA AAT TCA    1062
Ser Val Ser Ile Ser Ser Ala Val Lys Ser Ala Pro Glu Glu Asn Ser
        330             335             340

CGT GAA ATG ACA GAA ACG CAG ATG ATG ATA CAT TCC AAG TCT TCA AAT    1110
Arg Glu Met Thr Glu Thr Gln Met Met Ile His Ser Lys Ser Ser Asn
    345             350             355

GGA AAG TGAAATGGAT TGTATTTTGG TTTATAGTGA CGTAAACTGT ATGACAAACT    1166
Gly Lys ***
360

TTGCAGGACT TCCCTTATAA AGCAAAATAA TTGTTCAGCT TCCAATTAGT ATTCTTTTAT 1226

ATTTCTTTCA TTGGGCGCTT TCCCATCTCC AACTCGGAAG TAAGCCCAAG AGAACAACAT 1286

AAAGCAAACA ACATAAAGCA CAATAAAAAT GCAAATAAAT ATTTTCATTT TTATTTGTAA 1346
```

FIG.1B-3

```
ACGAATACAC CAAAAGGAGG CGCTCTTAAT AACTCCCAAT GTAAAAAGTT TTGTTTTAAT 1406

AAAAAATTAA TTATTATTCT TGCCAACAAA TGGCTAGAAA GGACTGAATA GATTATATAT 1466

TGCCAGATGT TAATACTGTA ACATACTTTT TAAATAACAT ATTTCTTAAA TCCAAATTTC 1526

TCTCAATGTT AGATTTAATT CCCTCAATAA CACCAATGTT TTGTTTTGTT TCGTTCTGGG 1586

TCATAAAACT TTGTTAAGGA ACTCTTTTGG AATAAAGAGC AGGATGCTGC GGAATTC    1643
```

FIG.1B-4

```
GAATTCCGCA GCC ATG ACC CCG CAG CTT CTC CTG GCC CTT GTC CTC TGG    49
           Met Thr Pro Gln Leu Leu Leu Ala Leu Val Leu Trp
            1           5                   10

GCC AGC TGC CCG CCC TGC AGT GGA AGG AAA GGG CCC CCA GCA GCT CTG    97
Ala Ser Cys Pro Pro Cys Ser Gly Arg Lys Gly Pro Pro Ala Ala Leu
         15              20                  25

ACA CTG CCC CGG GTG CAA TGC CGA GCC TCT CGG TAC CCG ATC GCC GTG   145
Thr Leu Pro Arg Val Gln Cys Arg Ala Ser Arg Tyr Pro Ile Ala Val
          30                  35                  40

GAT TGC TCC TGG ACC CTG CCG CCT GCT CCA AAC TCC ACC AGC CCC GTG   193
Asp Cys Ser Trp Thr Leu Pro Pro Ala Pro Asn Ser Thr Ser Pro Val
         45                  50          CHO ### ###       60
                                          55

TCC TTC ATT GCC ACG TAC AGG CTC GGC ATG GCT GCC CGG GGC CAC AGC   241
Ser Phe Ile Ala Thr Tyr Arg Leu Gly Met Ala Ala Arg Gly His Ser
                  65                  70                  75

TGG CCC TGC CTG CAG CAG ACG CCA ACG TCC ACC AGC TGC ACC ATC ACG   289
Trp Pro Cys Leu Gln Gln Thr Pro Thr Ser Thr Ser Cys Thr Ile Thr
             80                  85                  90

GAT GTC CAG CTG TTC TCC ATG GCT CCC TAC GTG CTC AAT GTC ACC GCC   337
Asp Val Gln Leu Phe Ser Met Ala Pro Tyr Val Leu Asn Val Thr Ala
              95                 100             105 CHO ### ###

GTC CAC CCC TGG GGC TCC AGC AGC AGC TTC GTG CCT TTC ATA ACA GAG   385
Val His Pro Trp Gly Ser Ser Ser Ser Phe Val Pro Phe Ile Thr Glu
         110             115                 120

CAC ATC ATC AAG CCC GAC CCT CCA GAA GGC GTG CGC CTA AGC CCC CTC   433
His Ile Ile Lys Pro Asp Pro Pro Glu Gly Val Arg Leu Ser Pro Leu
     125             130                 135                 140
```

FIG.5A

| | |
|---|---|
| GCT GAG CGC CAC GTA CAG GTG CAG TGG GAG CCT CCC GGG TCC TGG CCC | 481 |
| Ala Glu Arg His Val Gln Val Gln Trp Glu Pro Pro Gly Ser Trp Pro | |
|             145                150                155 | |
| TTC CCA GAG ATC TTC TCA CTG AAG TAC TGG ATC CGT TAC AAG CGT CAG | 529 |
| Phe Pro Glu Ile Phe Ser Leu Lys Tyr Trp Ile Arg Tyr Lys Arg Gln | |
|             160                165                170 | |
| GGA GCT GCG CGC TTC CAC CGG GTG GGG CCC ATT GAA GCC ACG TCC TTC | 577 |
| Gly Ala Ala Arg Phe His Arg Val Gly Pro Ile Glu Ala Thr Ser Phe | |
|             175                180                185 | |
| ATC CTC AGG GCT GTG CGG CCC CGA GCC AGG TAC TAC GTC CAA GTG GCG | 625 |
| Ile Leu Arg Ala Val Arg Pro Arg Ala Arg Tyr Tyr Val Gln Val Ala | |
|             190                195                200 | |
| GCT CAG GAC CTC ACA GAC TAC GGG GAA CTG AGT GAC TGG AGT CTC CCC | 673 |
| Ala Gln Asp Leu Thr Asp Tyr Gly Glu Leu Ser Asp Trp Ser Leu Pro | |
| 205                210                215                220 | |
| GCC ACT GCC ACA ATG AGC CTG GGC AAG TAGCAAGGGC TTCCCGCTGC | 720 |
| Ala Thr Ala Thr Met Ser Leu Gly Lys *** | |
|             225 | |
| CTCCAGACAG CACCTGGGTC CTCGCCACCC TAAGCCCCGG GACACCTGTT GGAGGGCGGA | 780 |
| TGGGATCTGC CTAGCCTGGG CTGGAGTCCT TGCTTTGCTG CTGCTGAGCT GCCGGGCAAC | 840 |
| CTCAGATGAC CGACTTTTCC CTTTGAGCCT CAGTTTCTCT AGCTGAGAAA TGGAGATGTA | 900 |
| CTACTCTCTC CTTTACCTTT ACCTTTACCA CAGTGCAGGG CTGACTGAAC TGTCACTGTG | 960 |

FIG.5B

```
AGATATTTTT TATTGTTTAA TTAGAAAAGA ATTGTTGTTG GGCTGGGCGC AGTGGATCGC  1020

ACCTGTAATC CCAGTCACTG GGAAGCCGAC GTGGGTGGGT AGCTTGAGGC CAGGAGCTCG  1080

AAACCAGTCC GGGCCACACA GCAAGACCCC ATCTCTAAAA AATTAATATA AATATAAAAT  1140

AAAAAAAAAA AAAAGGAATT C                                           1161
```

FIG.5C

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 2154 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: CDS
       (B) LOCATION: 64..1197

(xi) SEQUENCE DESCRIPTION: SEQ ID NO:1:

```
GGAATTCCGT AGTGCGAGGC CGGGCACAGC CTTCCTGTGT GGTTTTACCG CCCAGAGAGC          60

GTC ATG GAC CTG GGG AAA CCA ATG AAA AGC GTG CTG GTG GTG GCT CTC          108
    Met Asp Leu Gly Lys Pro Met Lys Ser Val Leu Val Val Ala Leu
    1               5                   10                  15

CTT GTC ATT TTC CAG GTA TGC CTG TGT CAA GAT GAG GTC ACG GAC GAT          156
Leu Val Ile Phe Gln Val Cys Leu Cys Gln Asp Glu Val Thr Asp Asp
                20                  25                  30

TAC ATC GGA GAC AAC ACC ACA GTG GAC TAC ACT TTG TTC GAG TCT TTG          204
Tyr Ile Gly Asp Asn Thr Thr Val Asp Tyr Thr Leu Phe Glu Ser Leu
            35                  40                  45

TGC TCC AAG AAG GAC GTG CGG AAC TTT AAA GCC TGG TTC CTC CCT ATC          252
Cys Ser Lys Lys Asp Val Arg Asn Phe Lys Ala Trp Phe Leu Pro Ile
        50                  55                  60

ATG TAC TCC ATC ATT TGT TTC GTG GGC CTA CTG GGC AAT GGG CTG GTC          300
Met Tyr Ser Ile Ile Cys Phe Val Gly Leu Leu Gly Asn Gly Leu Val
    65                  70                  75

GTG TTG ACC TAT ATC TAT TTC AAG AGG CTC AAG ACC ATG ACC GAT ACC          348
Val Leu Thr Tyr Ile Tyr Phe Lys Arg Leu Lys Thr Met Thr Asp Thr
80                  85                  90                  95

TAC CTG CTC AAC CTG GCG GTG GCA GAC ATC CTC TTC CTC CTG ACC CTT          396
Tyr Leu Leu Asn Leu Ala Val Ala Asp Ile Leu Phe Leu Leu Thr Leu
                100                 105                 110

CCC TTC TGG GCC TAC AGC GCG GCC AAG TCC TGG GTC TTC GGT GTC CAC          444
Pro Phe Trp Ala Tyr Ser Ala Ala Lys Ser Trp Val Phe Gly Val His
            115                 120                 125

TTT TGC AAG CTC ATC TTT GCC ATC TAC AAG ATG AGC TTC TTC AGT GGC          492
Phe Cys Lys Leu Ile Phe Ala Ile Tyr Lys Met Ser Phe Phe Ser Gly
        130                 135                 140

ATG CTC CTA CTT TTG TGC ATC AGC ATT GAC CGC TAC GTG GCC ATC GTC          540
Met Leu Leu Leu Cys Ile Ser Ile Asp Arg Tyr Val Ala Ile Val
    145                 150                 155

CAG GCT GTC TCA GCT CAC CGC CAC CGT GCC CGC GTC CTT CTC ATC AGC          588
Gln Ala Val Ser Ala His Arg His Arg Ala Arg Val Leu Leu Ile Ser
160                 165                 170                 175

AAG CTG TCC TGT GTG GGC AGC GCC ATA CTA GCC ACA GTG CTC TCC ATC          636
Lys Leu Ser Cys Val Gly Ser Ala Ile Leu Ala Thr Val Leu Ser Ile
                180                 185                 190

CCA GAG CTC CTG TAC AGT GAC CTC CAG AGG AGC AGC AGT GAG CAA GCG          684
Pro Glu Leu Leu Tyr Ser Asp Leu Gln Arg Ser Ser Ser Glu Gln Ala
            195                 200                 205

ATG CGA TGC TCT CTC ATC ACA GAG CAT GTG GAG GCC TTT ATC ACC ATC          732
```

```
Met Arg Cys Ser Leu Ile Thr Glu His Val Glu Ala Phe Ile Thr Ile
        210                 215                 220

CAG GTG GCC CAG ATG GTG ATC GGC TTT CTG GTC CCC CTG CTG GCC ATG      780
Gln Val Ala Gln Met Val Ile Gly Phe Leu Val Pro Leu Leu Ala Met
    225                 230                 235

AGC TTC TGT TAC CTT GTC ATC ATC CGC ACC CTG CTC CAG GCA CGC AAC      828
Ser Phe Cys Tyr Leu Val Ile Ile Arg Thr Leu Leu Gln Ala Arg Asn
240                 245                 250                 255

TTT GAG CGC AAC AAG GCC ATC AAG GTG ATC ATC GCT GTG GTC GTG GTC      876
Phe Glu Arg Asn Lys Ala Ile Lys Val Ile Ile Ala Val Val Val Val
                260                 265                 270

TTC ATA GTC TTC CAG CTG CCC TAC AAT GGG GTG GTC CTG GCC CAG ACG      924
Phe Ile Val Phe Gln Leu Pro Tyr Asn Gly Val Val Leu Ala Gln Thr
                275                 280                 285

GTG GCC AAC TTC AAC ATC ACC AGT AGC ACC TGT GAG CTC AGT AAG CAA      972
Val Ala Asn Phe Asn Ile Thr Ser Ser Thr Cys Glu Leu Ser Lys Gln
    290                 295                 300

CTC AAC ATC GCC TAC GAC GTC ACC TAC AGC CTG GCC TGC GTC CGC TGC     1020
Leu Asn Ile Ala Tyr Asp Val Thr Tyr Ser Leu Ala Cys Val Arg Cys
305                 310                 315

TGC GTC AAC CCT TTC TTG TAC GCC TTC ATC GGC GTC AAG TTC CGC AAC     1068
Cys Val Asn Pro Phe Leu Tyr Ala Phe Ile Gly Val Lys Phe Arg Asn
320                 325                 330                 335

GAT ATC TTC AAG CTC TTC AAG GAC CTG GGC TGC CTC AGC CAG GAG CAG     1116
Asp Ile Phe Lys Leu Phe Lys Asp Leu Gly Cys Leu Ser Gln Glu Gln
                340                 345                 350

CTC CGG CAG TGG TCT TCC TGT CGG CAC ATC CGG CGC TCC TCC ATG AGT     1164
Leu Arg Gln Trp Ser Ser Cys Arg His Ile Arg Arg Ser Ser Met Ser
                355                 360                 365

GTG GAG GCC GAG ACC ACC ACC ACC TTC TCC CCA TAGGCGACTC TTCTGCCTGG   1217
Val Glu Ala Glu Thr Thr Thr Thr Phe Ser Pro
                370                 375

ACTAGAGGGA CCTCTCCCAG GGTCCCTGGG GTGGGGATAG GGAGCAGATG CAATGACTCA   1277

GGACATCCCC CCGCCAAAAG CTGCTCAGGG GAAAAAGCAG CTCTCCCCTC AGAGTGCAAG   1337

CCCCTGCTCC AGAAGATAGC TTCACCCCAA TCCCAGCTAC CTCAACCAAT GCCAAAAAAA   1397

GACAGGGCTG ATAAGCTAAC ACCAGACAGA CAACACTGGG AAACAGAGGC TATTGTCCCC   1457

TAAACCAAAA ACTGAAAGTG AAAGTCCAGA AACTGTTCCC ACCTGCTGGA GTGAAGGGGC   1517

CAAGGAGGGT GAGTGCAAGG GGCGTGGGAG TGGCCTGAAG AGTCCTCTGA ATGAACCTTC   1577

TGGCCTCCCA CAGACTCAAA TGCTCAGACC AGCTCTTCCG AAAACCAGGC CTTATCTCCA   1637

AGACCAGAGA TAGTGGGGAG ACTTCTTGGC TTGGTGAGGA AAAGCGGACA TCAGCTGGTC   1697

AAACAAACTC TCTGAACCCC TCCCTCCATC GTTTTCTTCA CTGTCCTCCA AGCCAGCGGG   1757

AATGGCAGCT GCCACGCCGC CCTAAAAGCA CACTCATCCC CTCACTTGCC GCGTCGCCCT   1817

CCCAGGCTCT CAACAGGGGA GAGTGTGGTG TTTCCTGCAG GCCAGGCCAG CTGCCTCCGC   1877

GTGATCAAAG CCACACTCTG GGCTCCAGAG TGGGGATGAC ATGCACTCAG CTCTTGGCTC   1937

CACTGGGATG GGAGGAGAGG ACAAGGGAAA TGTCAGGGGC GGGGAGGGTG ACAGTGGCCG   1997

CCCAAGGCCA CGAGCTTGTT CTTTGTTCTT TGTCACAGGG ACTGAAAACC TCTCCTCATG   2057

TTCTGCTTTC GATTCGTTAA GAGAGCAACA TTTTACCCAC ACACAGATAA AGTTTTCCCT   2117

TGAGGAAACA ACAGCTTTAA AAAAAAAAAA GGAATTC                           2154
```

(2) INFORMATION FOR SEQ ID NO:2:

(i) SEQUENCE CHARACTERISTICS:

(A) LENGTH: 378 amino acids
(B) TYPE: amino acid
(D) TOPOLOGY: linear (ii) MOLECULE TYPE: protein (xi) SEQUENCE DESCRIPTION: SEQ ID NO:2:

```
Met Asp Leu Gly Lys Pro Met Lys Ser Val Leu Val Ala Leu Leu
 1               5                  10                  15

Val Ile Phe Gln Val Cys Leu Cys Gln Asp Glu Val Thr Asp Asp Tyr
                20                  25                  30

Ile Gly Asp Asn Thr Thr Val Asp Tyr Thr Leu Phe Glu Ser Leu Cys
                35                  40                  45

Ser Lys Lys Asp Val Arg Asn Phe Lys Ala Trp Phe Leu Pro Ile Met
 50                  55                  60

Tyr Ser Ile Ile Cys Phe Val Gly Leu Leu Gly Asn Gly Leu Val Val
 65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
                100                 105                 110

Phe Trp Ala Tyr Ser Ala Ala Lys Ser Trp Val Phe Gly Val His Phe
         115                 120                 125

Cys Lys Leu Ile Phe Ala Ile Tyr Lys Met Ser Phe Phe Ser Gly Met
 130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ser Ala Ile Leu Ala Thr Val Leu Ser Ile Pro
                180                 185                 190

Glu Leu Leu Tyr Ser Asp Leu Gln Arg Ser Ser Glu Gln Ala Met
            195                 200                 205

Arg Cys Ser Leu Ile Thr Glu His Val Glu Ala Phe Ile Thr Ile Gln
 210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
                260                 265                 270

Ile Val Phe Gln Leu Pro Tyr Asn Gly Val Val Leu Ala Gln Thr Val
         275                 280                 285

Ala Asn Phe Asn Ile Thr Ser Ser Thr Cys Glu Leu Ser Lys Gln Leu
 290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Ile Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
         355                 360                 365

Glu Ala Glu Thr Thr Thr Thr Phe Ser Pro
370                 375
```

(2) INFORMATION FOR SEQ ID NO:3:

(i) SEQUENCE CHARACTERISTICS:
        (A) LENGTH: 1643 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 34..1116

(xi) SEQUENCE DESCRIPTION: SEQ ID NO:3:

```
GGAATTCCCT GATATACACC TGGACCACCA CCA ATG GAT ATA CAA ATG GCA AAC        54
                                    Met Asp Ile Gln Met Ala Asn
                                     1               5

AAT TTT ACT CCG CCC TCT GCA ACT CCT CAG GGA AAT GAC TGT GAC CTC        102
Asn Phe Thr Pro Pro Ser Ala Thr Pro Gln Gly Asn Asp Cys Asp Leu
        10                  15                  20

TAT GCA CAT CAC AGC ACG GCC AGG ATA GTA ATG CCT CTG CAT TAC AGC        150
Tyr Ala His His Ser Thr Ala Arg Ile Val Met Pro Leu His Tyr Ser
 25                  30                  35

CTC GTC TTC ATC ATT GGG CTC GTG GGA AAC TTA CTA GCC TTG GTC GTC        198
Leu Val Phe Ile Ile Gly Leu Val Gly Asn Leu Leu Ala Leu Val Val
 40                  45                  50                  55

ATT GTT CAA AAC AGG AAA AAA ATC AAC TCT ACC ACC CTC TAT TCA ACA        246
Ile Val Gln Asn Arg Lys Lys Ile Asn Ser Thr Thr Leu Tyr Ser Thr
                 60                  65                  70

AAT TTG GTG ATT TCT GAT ATA CTT TTT ACC ACG GCT TTG CCT ACA CGA        294
Asn Leu Val Ile Ser Asp Ile Leu Phe Thr Thr Ala Leu Pro Thr Arg
            75                  80                  85

ATA GCC TAC TAT GCA ATG GGC TTT GAC TGG AGA ATC GGA GAT GCC TTG        342
Ile Ala Tyr Tyr Ala Met Gly Phe Asp Trp Arg Ile Gly Asp Ala Leu
        90                  95                 100

TGT AGG ATA ACT GCG CTA GTG TTT TAC ATC AAC ACA TAT GCA GGT GTG        390
Cys Arg Ile Thr Ala Leu Val Phe Tyr Ile Asn Thr Tyr Ala Gly Val
105                 110                 115

AAC TTT ATG ACC TGC CTG AGT ATT GAC CGC TTC ATT GCT GTG GTG CAC        438
Asn Phe Met Thr Cys Leu Ser Ile Asp Arg Phe Ile Ala Val Val His
120                 125                 130                 135

CCT CTA CGC TAC AAC AAG ATA AAA AGG ATT GAA CAT GCA AAA GGC GTG        486
Pro Leu Arg Tyr Asn Lys Ile Lys Arg Ile Glu His Ala Lys Gly Val
                140                 145                 150

TGC ATA TTT GTC TGG ATT CTA GTA TTT GCT CAG ACA CTC CCA CTC CTC        534
Cys Ile Phe Val Trp Ile Leu Val Phe Ala Gln Thr Leu Pro Leu Leu
            155                 160                 165

ATC AAC CCT ATG TCA AAG CAG GAG GCT GAA AGG ATT ACA TGC ATG GAG        582
Ile Asn Pro Met Ser Lys Gln Glu Ala Glu Arg Ile Thr Cys Met Glu
        170                 175                 180

TAT CCA AAC TTT GAA GAA ACT AAA TCT CTT CCC TGG ATT CTG CTT GGG        630
Tyr Pro Asn Phe Glu Glu Thr Lys Ser Leu Pro Trp Ile Leu Leu Gly
    185                 190                 195

GCA TGT TTC ATA GGA TAT GTA CTT CCA CTT ATA ATC ATT CTC ATC TGC        678
Ala Cys Phe Ile Gly Tyr Val Leu Pro Leu Ile Ile Ile Leu Ile Cys
200                 205                 210                 215

TAT TCT CAG ATC TGC TGC AAA CTC TTC AGA ACT GCC AAA CAA AAC CCA        726
Tyr Ser Gln Ile Cys Cys Lys Leu Phe Arg Thr Ala Lys Gln Asn Pro
                220                 225                 230

CTC ACT GAG AAA TCT GGT GTA AAC AAA AAG GCT CTC AAC ACA ATT ATT        774
```

```
Leu Thr Glu Lys Ser Gly Val Asn Lys Lys Ala Leu Asn Thr Ile Ile
            235                 240                 245

CTT ATT ATT GTT GTG TTT GTT CTC TGT TTC ACA CCT TAC CAT GTT GCA      822
Leu Ile Ile Val Val Phe Val Leu Cys Phe Thr Pro Tyr His Val Ala
        250                 255                 260

ATT ATT CAA CAT ATG ATT AAG AAG CTT CGT TTC TCT AAT TTC CTG GAA      870
Ile Ile Gln His Met Ile Lys Lys Leu Arg Phe Ser Asn Phe Leu Glu
        265                 270                 275

TGT AGC CAA AGA CAT TCG TTC CAG ATT TCT CTG CAC TTT ACA GTA TGC      918
Cys Ser Gln Arg His Ser Phe Gln Ile Ser Leu His Phe Thr Val Cys
280                 285                 290                 295

CTG ATG AAC TTC AAT TGC TGC ATG GAC CCT TTT ATC TAC TTC TTT GCA      966
Leu Met Asn Phe Asn Cys Cys Met Asp Pro Phe Ile Tyr Phe Phe Ala
                300                 305                 310

TGT AAA GGG TAT AAG AGA AAG GTT ATG AGG ATG CTG AAA CGG CAA GTC     1014
Cys Lys Gly Tyr Lys Arg Lys Val Met Arg Met Leu Lys Arg Gln Val
            315                 320                 325

AGT GTA TCG ATT TCT AGT GCT GTG AAG TCA GCC CCT GAA GAA AAT TCA     1062
Ser Val Ser Ile Ser Ser Ala Val Lys Ser Ala Pro Glu Glu Asn Ser
        330                 335                 340

CGT GAA ATG ACA GAA ACG CAG ATG ATG ATA CAT TCC AAG TCT TCA AAT     1110
Arg Glu Met Thr Glu Thr Gln Met Met Ile His Ser Lys Ser Ser Asn
        345                 350                 355

GGA AAG TGAAATGGAT TGTATTTTGG TTTATAGTGA CGTAAACTGT ATGACAAACT     1166
Gly Lys
360

TTGCAGGACT TCCCTTATAA AGCAAAATAA TTGTTCAGCT TCCAATTAGT ATTCTTTTAT   1226

ATTTCTTTCA TTGGGCGCTT TCCCATCTCC AACTCGGAAG TAAGCCCAAG AGAACAACAT   1286

AAAGCAAACA ACATAAAGCA CAATAAAAAT GCAAATAAAT ATTTTCATTT TTATTTGTAA   1346

ACGAATACAC CAAAAGGAGG CGCTCTTAAT AACTCCCAAT GTAAAAGTT TTGTTTTAAT    1406

AAAAAATTAA TTATTATTCT TGCCAACAAA TGGCTAGAAA GGACTGAATA GATTATATAT   1466

TGCCAGATGT TAATACTGTA ACATACTTTT TAAATAACAT ATTTCTTAAA TCCAAATTTC   1526

TCTCAATGTT AGATTTAATT CCCTCAATAA CACCAATGTT TTGTTTTGTT TCGTTCTGGG   1586

TCATAAAACT TTGTTAAGGA ACTCTTTTGG AATAAAGAGC AGGATGCTGC GGAATTC      1643

(2) INFORMATION FOR SEQ ID NO:4:

(i) SEQUENCE CHARACTERISTICS:
        (A) LENGTH: 361 amino acids
        (B) TYPE: amino acid
        (D) TOPOLOGY: linear (ii) MOLECULE TYPE: protein (xi) SEQUENCE DESCRIPTION: SEQ ID NO:4:

Met Asp Ile Gln Met Ala Asn Asn Phe Thr Pro Pro Ser Ala Thr Pro
  1               5                  10                  15

Gln Gly Asn Asp Cys Asp Leu Tyr Ala His His Ser Thr Ala Arg Ile
             20                  25                  30

Val Met Pro Leu His Tyr Ser Leu Val Phe Ile Ile Gly Leu Val Gly
         35                  40                  45

Asn Leu Leu Ala Leu Val Val Ile Val Gln Asn Arg Lys Lys Ile Asn
     50                  55                  60

Ser Thr Thr Leu Tyr Ser Thr Asn Leu Val Ile Ser Asp Ile Leu Phe
 65                  70                  75                  80

Thr Thr Ala Leu Pro Thr Arg Ile Ala Tyr Tyr Ala Met Gly Phe Asp
```

```
                      85                  90                      95
Trp Arg Ile Gly Asp Ala Leu Cys Arg Ile Thr Ala Leu Val Phe Tyr
                100                 105                 110
Ile Asn Thr Tyr Ala Gly Val Asn Phe Met Thr Cys Leu Ser Ile Asp
            115                 120                 125
Arg Phe Ile Ala Val Val His Pro Leu Arg Tyr Asn Lys Ile Lys Arg
        130                 135                 140
Ile Glu His Ala Lys Gly Val Cys Ile Phe Val Trp Ile Leu Val Phe
145                 150                 155                 160
Ala Gln Thr Leu Pro Leu Leu Ile Asn Pro Met Ser Lys Gln Glu Ala
                165                 170                 175
Glu Arg Ile Thr Cys Met Glu Tyr Pro Asn Phe Glu Glu Thr Lys Ser
            180                 185                 190
Leu Pro Trp Ile Leu Leu Gly Ala Cys Phe Ile Gly Tyr Val Leu Pro
        195                 200                 205
Leu Ile Ile Ile Leu Ile Cys Tyr Ser Gln Ile Cys Cys Lys Leu Phe
210                 215                 220
Arg Thr Ala Lys Gln Asn Pro Leu Thr Glu Lys Ser Gly Val Asn Lys
225                 230                 235                 240
Lys Ala Leu Asn Thr Ile Ile Leu Ile Ile Val Val Phe Val Leu Cys
                245                 250                 255
Phe Thr Pro Tyr His Val Ala Ile Ile Gln His Met Ile Lys Lys Leu
            260                 265                 270
Arg Phe Ser Asn Phe Leu Glu Cys Ser Gln Arg His Ser Phe Gln Ile
        275                 280                 285
Ser Leu His Phe Thr Val Cys Leu Met Asn Phe Asn Cys Cys Met Asp
290                 295                 300
Pro Phe Ile Tyr Phe Phe Ala Cys Lys Gly Tyr Lys Arg Lys Val Met
305                 310                 315                 320
Arg Met Leu Lys Arg Gln Val Ser Val Ser Ile Ser Ser Ala Val Lys
                325                 330                 335
Ser Ala Pro Glu Glu Asn Ser Arg Glu Met Thr Glu Thr Gln Met Met
            340                 345                 350
Ile His Ser Lys Ser Ser Asn Gly Lys
        355                 360

(2) INFORMATION FOR SEQ ID NO:5:

(i) SEQUENCE CHARACTERISTICS:
        (A) LENGTH: 1161 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 14..703

(xi) SEQUENCE DESCRIPTION: SEQ ID NO:5:

GAATTCCGCA GCC ATG ACC CCG CAG CTT CTC CTG GCC CTT GTC CTC TGG        49
            Met Thr Pro Gln Leu Leu Leu Ala Leu Val Leu Trp
              1               5                  10

GCC AGC TGC CCG CCC TGC AGT GGA AGG AAA GGG CCC CCA GCA GCT CTG       97
Ala Ser Cys Pro Pro Cys Ser Gly Arg Lys Gly Pro Pro Ala Ala Leu
         15                  20                  25

ACA CTG CCC CGG GTG CAA TGC CGA GCC TCT CGG TAC CCG ATC GCC GTG      145
```

```
Thr Leu Pro Arg Val Gln Cys Arg Ala Ser Arg Tyr Pro Ile Ala Val
         30                  35                  40

GAT TGC TCC TGG ACC CTG CCG CCT GCT CCA AAC TCC ACC AGC CCC GTG        193
Asp Cys Ser Trp Thr Leu Pro Pro Ala Pro Asn Ser Thr Ser Pro Val
 45                  50                  55                  60

TCC TTC ATT GCC ACG TAC AGG CTC GGC ATG GCT GCC CGG GGC CAC AGC        241
Ser Phe Ile Ala Thr Tyr Arg Leu Gly Met Ala Ala Arg Gly His Ser
                     65                  70                  75

TGG CCC TGC CTG CAG CAG ACG CCA ACG TCC ACC AGC TGC ACC ATC ACG        289
Trp Pro Cys Leu Gln Gln Thr Pro Thr Ser Thr Ser Cys Thr Ile Thr
                 80                  85                  90

GAT GTC CAG CTG TTC TCC ATG GCT CCC TAC GTG CTC AAT GTC ACC GCC        337
Asp Val Gln Leu Phe Ser Met Ala Pro Tyr Val Leu Asn Val Thr Ala
             95                 100                 105

GTC CAC CCC TGG GGC TCC AGC AGC AGC TTC GTG CCT TTC ATA ACA GAG        385
Val His Pro Trp Gly Ser Ser Ser Ser Phe Val Pro Phe Ile Thr Glu
        110                 115                 120

CAC ATC ATC AAG CCC GAC CCT CCA GAA GGC GTG CGC CTA AGC CCC CTC        433
His Ile Ile Lys Pro Asp Pro Pro Glu Gly Val Arg Leu Ser Pro Leu
125                 130                 135                 140

GCT GAG CGC CAG CTA CAG GTG CAG TGG GAG CCT CCC GGG TCC TGG CCC        481
Ala Glu Arg Gln Leu Gln Val Gln Trp Glu Pro Pro Gly Ser Trp Pro
                145                 150                 155

TTC CCA GAG ATC TTC TCA CTG AAG TAC TGG ATC CGT TAC AAG CGT CAG        529
Phe Pro Glu Ile Phe Ser Leu Lys Tyr Trp Ile Arg Tyr Lys Arg Gln
            160                 165                 170

GGA GCT GCG CGC TTC CAC CGG GTG GGG CCC ATT GAA GCC ACG TCC TTC        577
Gly Ala Ala Arg Phe His Arg Val Gly Pro Ile Glu Ala Thr Ser Phe
        175                 180                 185

ATC CTC AGG GCT GTG CGG CCC CGA GCC AGG TAC TAC GTC CAA GTG GCG        625
Ile Leu Arg Ala Val Arg Pro Arg Ala Arg Tyr Tyr Val Gln Val Ala
    190                 195                 200

GCT CAG GAC CTC ACA GAC TAC GGG GAA CTG AGT GAC TGG AGT CTC CCC        673
Ala Gln Asp Leu Thr Asp Tyr Gly Glu Leu Ser Asp Trp Ser Leu Pro
205                 210                 215                 220

GCC ACT GCC ACA ATG AGC CTG GGC AAG TAGCAAGGGC TTCCCGCTGC              720
Ala Thr Ala Thr Met Ser Leu Gly Lys
                225                 230

CTCCAGACAG CACCTGGGTC CTCGCCACCC TAAGCCCCGG GACACCTGTT GGAGGGCGGA      780

TGGGATCTGC CTAGCCTGGG CTGGAGTCCT TGCTTTGCTG CTGCTGAGCT GCCGGGCAAC      840

CTCAGATGAC CGACTTTTCC CTTTGAGCCT CAGTTTCTCT AGCTGAGAAA TGGAGATGTA      900

CTACTCTCTC CTTTACCTTT ACCTTTACCA CAGTGCAGGG CTGACTGAAC TGTCACTGTG      960

AGATATTTTT TATTGTTTAA TTAGAAAAGA ATTGTTGTTG GGCTGGGCGC AGTGGATCGC     1020

ACCTGTAATC CCAGTCACTG GGAAGCCGAC GTGGGTGGGT AGCTTGAGGC CAGGAGCTCG     1080

AAACCAGTCC GGGCCACACA GCAAGACCCC ATCTCTAAAA AATTAATATA AATATAAAAT     1140

AAAAAAAAAA AAAAGGAATT C                                               1161

(2) INFORMATION FOR SEQ ID NO:6:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO:6:
```

-continued

```
Met Thr Pro Gln Leu Leu Leu Ala Leu Val Leu Trp Ala Ser Cys Pro
 1               5                  10                 15

Pro Cys Ser Gly Arg Lys Gly Pro Pro Ala Ala Leu Thr Leu Pro Arg
                 20              25                  30

Val Gln Cys Arg Ala Ser Arg Tyr Pro Ile Ala Val Asp Cys Ser Trp
         35              40                  45

Thr Leu Pro Pro Ala Pro Asn Ser Thr Ser Pro Val Ser Phe Ile Ala
     50              55                  60

Thr Tyr Arg Leu Gly Met Ala Ala Arg Gly His Ser Trp Pro Cys Leu
 65                  70              75                      80

Gln Gln Thr Pro Thr Ser Thr Ser Cys Thr Ile Thr Asp Val Gln Leu
             85                  90                  95

Phe Ser Met Ala Pro Tyr Val Leu Asn Val Thr Ala Val His Pro Trp
             100                 105                110

Gly Ser Ser Ser Ser Phe Val Pro Phe Ile Thr Glu His Ile Ile Lys
             115                 120                 125

Pro Asp Pro Pro Glu Gly Val Arg Leu Ser Pro Leu Ala Glu Arg Gln
     130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                 165                 170                 175

Phe His Arg Val Gly Pro Ile Glu Ala Thr Ser Phe Ile Leu Arg Ala
                 180                 185                 190

Val Arg Pro Arg Ala Arg Tyr Tyr Val Gln Val Ala Ala Gln Asp Leu
         195                 200                 205

Thr Asp Tyr Gly Glu Leu Ser Asp Trp Ser Leu Pro Ala Thr Ala Thr
     210                 215                 220

Met Ser Leu Gly Lys
225
```

EPSTEIN BARR VIRUS INDUCED GENES

This application is a divisional application of Ser. No. 08/352,678 filed Nov. 30, 1994, now U.S. Pat. No. 6,043, 351 which is a continuation of Ser. No. 07/980,518, filed Nov. 25, 1992, now abandoned.

STATEMENT OF GOVERNMENT RIGHTS IN THE INVENTION

Part of the work performed during development of this invention utilized U.S. Government funds. The U.S. Government has certain rights in this invention.

BACKGROUND OF THE INVENTION

1. Field of the Invention

The present invention relates, in general, to Epstein Barr virus induced (EBI) genes. In particular, the present invention relates to DNA segments coding for EBI 1, EBI 2, or EBI 3 polypeptides; EBI 1, EBI 2, or EBI 3 polypeptides; recombinant DNA molecules; cells containing the recombinant DNA molecules; antisense EBI 1, EBI 2, or EBI 3 constructs; antibodies having binding affinity to an EBI 1, EBI 2, or EBI 3 polypeptide; hybridomas containing the antibodies; nucleic acid probes for the detection of the presence of Epstein Barr Virus; a method of detecting Epstein Barr virus in a sample; and kits containing nucleic acid probes or antibodies.

2. Background Information

Epstein-Barr Virus (EBV) is the cause of infectious mononucleosis, a benign proliferation of infected B lymphocytes (Henle, G., et al., Proc. Natl. Acad. Sci. USA 59(1):94–101 (1968)) and can also cause acute and rapidly progressive B lymphoproliferative disease in severely immune compromised patients or in experimental infection of tamarins (Miller, G., Fields Virol., 2nd ed., 1921–58 (1990)). Infection of human B lymphocytes, in vitro, results in expression of six virus encoded nuclear proteins (EBNAs) and two virus encoded membrane proteins (LMPs) (Kieff and Liebowitz, Fields Virol., 2nd ed., 1889–1920 (1990)), and in substantially altered cell growth (Nilsson and Klein, Adv. Cancer Res. 37(319):319–80 (1982)). EBV infected B lymphocytes recapitulate features of antigen stimulation in enlarging, increasing RNA synthesis, expressing activation antigens and adhesion molecules, secreting Ig and proliferating (Boyd, A. W., et al., J. Immunol. 134(3):1516–23 (1985); Gordon, J., et al., Inununology 58(4):591–5 (1986); Guy and Gordon, Intl. J. Cancer 43(4):703–8 (1989); Nilsson and Klein, Adv. Cancer Res. 37(319):319–80 (1982); Thorley-Lawson, D. A., et al., J. Immunol. 134(5):3007–12 (1985)). Unlike antigen stimulated B lymphocytes, EBV infected B lymphocytes continue to proliferate in vitro as immortalized lymphoblastoid cell lines (LCLs) (Nilsson, K., et al., Intl. J. Cancer 8(3):443–50 (1971)).

EBV effects on lymphocytes have been studied by comparing the properties of EBV-negative [EBV(−)] Burkitt lymphoma (BL) cell lines and EBV-positive [EBV(+)] derivatives, infected by EBV, in vitro (Calender, A., et al., Proc. Natl. Acad. Sci. USA 84(22):8060–4 (1987); Ehlin-Henriksson, B., et al., Intl. J. Cancer 39(2):211–8 (1987); Nilsson and Klein, Adv. Cancer Res. 37(319):319–80 (1982); Rowe, M., et al., Intl. J. Cancer 37(3):367–73 (1986)). EBV(−) BL cells resemble proliferating centroblasts of germinal centers, characteristically expressing CD10, CD20, CD77 (BLA), class II antigen, and the carbohydrate recognized by peanut agglutinin (Calender, A., et al., Proc. Natl. Acad. Sci. USA 84(22):8060–4 (1987); Ehlin-Henriksson, B., et al., Intl. J. Cancer 39(2):211–8 (1987); Favrot, M. C., et al., Intl. J. Cancer 38(6):901–6 (1986); Gregory, C. D., et al., Intl. J. Cancer 42(2):213–20 (1988); Gregory, C. D., et al., J. Gen. Virol. 71:1481–1495 (1990); Gregory, C. D., et al., J. Immunol. 139(1):313–8 (1987); Rowe, M., et al., Intl. J. Cancer 37(3):367–73 (1986); Rowe, M., et al., Intl. J. Cancer 35(4):435–41 (1985)). Both EBV(−) BL cells and centroblasts lack surface IgD and antigens associated with early phases of mitogen stimulation in vitro, including CD23, CD39 and CD30. In general, EBV(+) BL cells closely resemble EBV infected primary B lymphocytes in not expressing CD10 or CD77 and in expressing early activation and differentiation markers, vimentin, Bac-1, Bcl-2, surface IgD and CD44 (Calender, A., et al., Proc. Natl. Acad. Sci. USA 84(22):8060–4 (1987); Ehlin-Henriksson, B., et al., Intl. J. Cancer 39(2):211–8 (1987); Favrot, M. C., et al., Intl. J. Cancer 38(6):901–6 (1986); Gregory, C. D., et al., J. Gen. Virol. 71:1481–1495 (1990); Henderson, S., et al., Cell 65(7):1107–15 (1991); Rowe, M., et al., Intl. J. Cancer 37(3):367–73 (1986); Rowe, M., et al., EMBO J. 6(9):2743–51 (1987); Spira, G., et al., J. Immunol. 126(1):122–6 (1981); Suzuki, T., et al., J. Immunol. 137(4):1208–13 (1986)). Experiments with single gene transfer into EBV(−) B lymphoma cells, or with specifically mutated EBV recombinants reveal that EBNA 2, LMP 1 and EBNA 3C are essential for lymphocyte growth transformation and alter cellular or viral gene expression. Expression of EBNA 2 alone in EBV(−) BL cell lines results in enhanced transcription of CD23, CD21 (Cordier, M., et al., J. Virol. 64(3):1002–13 (1990); Wang, F., et al., J. Virol. 64(5):2309–18 (1990); Wang, F., et al., Proc. Natl. Acad. Sci. USA 84(10):3452–6 (1987)), and c-fgr (Knutson, J. C., J. Virol. 64(6):2530–6 (1990)). EBNA 2 also transactivates the LMP promoters (Fahraeus, R., et al., Proc. Natl. Acad. Sci. USA 87(19):7390–4 (1990); Wang, F., et al., J. Virol. 64(7):3407–16 (1990)). Analysis of a series of EBNA 2 mutants indicates that the ability of EBNA 2 to transactivate gene expression is tightly linked to its essential role in cell growth transformation (Cohen, J. I., et al., J. Virol. 65(5):2545–54 (1991)). LMP 1 is also critical to EBV's effects on cell growth. LMP 1 transforms immortalized rodent fibroblasts (Baichwal and Sugden, Oncogene 2(5):461–7 (1988); Wang, D., et al., Cell 43:831–40 (1985)) and induces vimentin, Bcl-2 and many of the activation markers and adhesion molecules that EBV induces in BL cells (Birkenbach, M., et al., J. Virol. 63(9):4079–84 (1989); Henderson, S., et al., Cell 65(7): 1107–15 (1991); Wang, D., et al., J. Virol. 62(11):4173–84 (1988)). In EBV(−) BL cells, EBNA 3c induces higher level expression of CD21 (Wang, F., et al., J. Virol. 64(5):2309–18 (1990)).

Since altered B lymphocyte gene expression is a central theme in EBV induced changes in B lymphocyte growth, a more complete description of the repertoire of EBV induced genes would be advantageous prior to the investigation of specific genes for their role as mediators of EBV effects on cell growth. Also, because of the similar effects of EBV and antigen, EBV induced genes are likely to include mediators of antigen induced B lymphocyte growth or differentiation. Previously, recognition of such genes has been largely based on increased expression of lymphocyte surface markers (Calender, A., et al., Proc. Natl. Acad. Sci. USA 84(22):8060–4 (1987)), defined by monoclonal antibodies derived against EBV or antigen activated B lymphocytes. Few of these surface markers are likely candidates for important effectors of EBV or antigen induced alterations in lymphocyte growth. The experiments described here use subtractive hybridization to identify cDNA clones of RNAs which are more abundant in an in vitro infected EBV(+) BL cell than in the non-infected EBV(−) control BL cell.

SUMMARY OF THE INVENTION

It is a general object of this invention to provide EBI 1, EBI 2, and EBI 3 DNA segments. It is a specific object of this invention to provide a DNA segment coding for a polypeptide having an amino acid sequence corresponding to an EBI 1, EBI 2, or EBI 3 polypeptide.

It is another object of the invention to provide a substantially pure polypeptide having an amino acid sequence corresponding to an EBI 1, EBI 2, or EBI 3 polypeptide.

It is a further object of the invention to provide a nucleic acid probe for the detection of the presence of Epstein Barr Virus in a sample.

It is another object of the invention to provide a method of detecting Epstein Barr Virus in a sample.

It is a further object of the invention to provide a kit for identifying or amplifying a gene encoding an EBI 1, EBI 2, or EBI 3 polypeptide.

It is another object of the invention to provide a DNA molecule comprising, 5' to 3', a promoter effective to initiate transcription in a cell and an EBI 1, EBI 2, or EBI 3 DNA segment.

It is a further object of the invention to provide a recombinant DNA molecule comprising a vector and an EBI 1, EBI 2, or EBI 3 DNA segment.

It is a further object of the invention to provide a DNA molecule comprising a transcriptional region functional in a cell, a sequence complimentary to an RNA sequence encoding an amino acid sequence corresponding to an EBI 1, EBI 2, or EBI 3 polypeptide, and a transcriptional termination region functional in said cell.

It is another object of the invention to provide cells containing the above-described DNA molecules.

It is a further object of the invention to provide an antibody having binding affinity to an EBI 1, EBI 2, or EBI 3 polypeptide, or a binding fragment thereof.

It is another object of the invention to provide a hybridoma which produces the above-described antibody, or binding fragment thereof.

It is a further object of the invention to provide a method of detecting an EBI 1, EBI 2, or EBI 3 polypeptide in a sample.

It is another object of the invention to provide a diagnostic kit comprising EBI 1, EBI 2, or EBI 3 antibodies.

Further objects and advantages of the present invention will be clear from the description that follows.

BRIEF DESCRIPTION OF THE DRAWINGS

FIGS. 1A-1 to 1A-4; 1B-1 to 1B-4. EBV induced gene (EBI) 1 and 2 RNA: Nucleotide and deduced amino acid sequences. (1A) EBI 1 has two potential translational initiation codons. In frame stop codons are indicated asterisks (*). A hydrophobic amino terminal segment (single underline) is predicted to be a signal peptide for membrane translocation. Seven other highly hydrophobic segments are predicted to form membrane spanning domains and are delineated by double underlines. Potential asparagine linked glycosylation sites (CHO######) are present in the extracellular amino terminal segment and third extracellular loop. The sequence motif S-(I/V)-D-R-(Y/F)-X-X-X-X (where X represents consecutive hydrophobic residues), is highly conserved among a large number of G-protein coupled receptors and is indicated at the end of the third transmembrane domain (::::). (1B) EBI 2 has 2 possible initiator methionine codons. Predicted transmembrane domains are indicated (double underlines). No signal peptide sequence was identified. The amino terminal extracellular segment contains a potential N-linked glycosylation site (CHO######).

FIG. 2. RNA blot hybridization analysis of EBV induced cellular gene expression. Polyadenylylated (4 to 12 μg per lane) was size fractionated on formaldehyde agarose gels, transferred to charged nylon membranes, and hybridized with the probes indicated at the bottom of each autoradiograph panel. RNA samples used are indicated at the top of each lane (LCL:EBV immortalized primary B lymphoblastoid cell line, IB4; BL:EBV negative Burkitt lymphoma cell line, BL41; EBL:EBV infected Burkitt lymphoma cell line, BL41/B95-8, derived by in vitro infection of BL41 line). Dashes indicate positions of ribosomal RNA bands (18s, 28s). The band detected at 1.5 kb in the LCL lane by the P68 probe is due to residual signal from a prior hybridization.

FIG. 3. Expression of EBI 1 and EBI 2 receptor genes in human lymphoid tissues and cell lines. 32P-labelled probes indicated at the left of each panel were hybridized to blots containing RNA from the cell lines indicated at the top of each lane. BL41 and BL30 are EBV-negative BL cell lines; BL41/P3HR1 is infected with a non-transforming EBV strain, p3HR1; BL41/B95-8 is infected with a transforming EBV strain; IB4 is a cell line derived by infecting primary B lymphocytes with EBV of the B95-8 strain; LCL-W91 is a recently established cell line transformed with EBV strain W91; TONSIL is unfractionated cells from surgically excised human tonsil; PBMC is unfractionated peripheral blood mononuclear cells; PBMC PWM is PBMC stimulated 72 h with pokeweed mitogen (2.5 μg/ml); PBT PHA is T cells purified from PBMC by sheep erythrocyte rosetting, stimulated 72 h with phytohemagglutinin (1 μg/ml); B MARR is post-mortem bone marrow; SPLEEN is unfractionated cells from surgically excised spleen; HL60 is a promyelocytic leukemia cell line; U937 is a monocytic leukemia cell line; K562 is a chronic myelogenous leukemia cell line; JURKAT is a T cell leukemia cell line; HSB-2 is a T cell acute lymphoblastic leukemia cell line; RHEK-1 is an adenovirus/SV40 transformed human keratinocyte; TK143 is a osteosarcoma cell line. Each panel is a composite prepared from autoradiographs of two separate blots for each probe.

FIG. 4. EBI 1 and EBI 2 gene expression in human tissues. EBI 1, EBI 2 and immunoglobulin mu chain (IgU) probes were hybridized to RNA samples from the following human tissues: heart (HE), brain (BR), placenta (PL), lung (LU), liver (LI), kidney (KI), skeletal muscle (SM) and pancreas (PA). Numbers at the left indicate positions and sizes (in kb) of RNA markers. Specific RNA bands are indicated by arrows to the right of each panel. The EBI 1 probe detects faint 2.4 kb bands in lung and pancreas PNA. The EBI 2 probe detects an abundant 1.9 kb RNA in lung, and a faint 1.9 kb band in pancreas. The 2.7 kb IgU RNA is detected in lung, liver and pancreas preparations. The 1.5 kb band in placental RNA hybridized with IgU probe is residual signal from a previous hybridization.

FIGS. 5A–C. Complete nucleotide and deduced amino acid sequences of EBI 3 cDNA. The 1164 nucleotide EBI 3 cDNA contains a 690 nucleotide open reading frame encoding a 26 kD polypeptide. A hydrophobic amino terminal segment (bold underline) comprises a signal peptide for membrane translocation. No other hydrophobic segments that could potentially form a transmembrane domain are evident. Two potential asparagine-linked glycosylation sites are indicated (CHO###). The nucleotide sequence of the 3' untranslated region bears significant homology with the human Alu repeat element (light underline).

Figure 2:
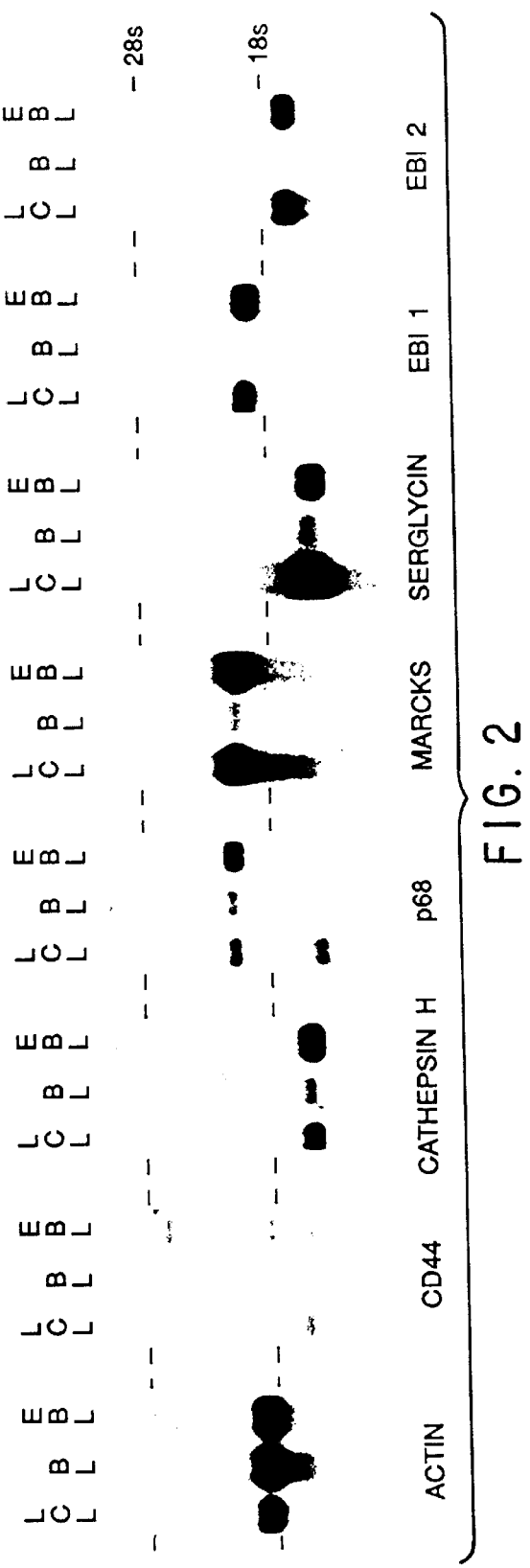

(A) EBI 3 or actin probes were hybridized to blots containing RNA from the cell lines or lymphoid tissues indicated at the top of each lane. (BL41 and BL30 are EBV(–) Burkitt lymphoma cell lines; BL41/P3HR1 is infected with the non-transforming P3HR1 strain of EBV; BL41/B95-8 is infected with the transforming, B95-8 strain of EBV; IB4 is a lympohblastoid cell line generated by transformation of primary B lymphocytes with B95-8 virus; LCL-W91 EBV strain; TONSIL represents unfractionated cells from surgically excised human tonsil; PBMC is unfractionated peripheral blood mononuclear cells; PBMC-PWM is PBMC stimulated 72 h with pokeweed mitogen (2.5 µg/ml); PBT-PHA is T cells purified from PBMC by sheep erythrocyte rosetting, stimulated 72 h with phytohemagglutinin (1.0 µg/mL); B MARR is post-mortem costal bone marrow; SPLEEN is unfractionated cells from surgically excised normal human spleen; HL60 is a promyelocytic leukemia cell line; U937 is a histiocytic lymphoma cell line with monocyte features; K562 is a chronic myelogenous leukemia cell line; Jurkat is a T cell leukemia; TK143 is an osteosarcoma line. Each autoradiographic panel was generated from two separate blots.

(B) EBI 3 was hybridized to a commercially prepared blot (Multiple Tissue Northern, Clontech, Calif.) containing polyadenylated RNA (2 µg/lane) from each of the following human tissues: heart (HE), brain BR), placenta (PL), lung (LU), liver (LI), kidney (KI), skeletal muscle (SM) and pancreas (PA). The EBI 3 probe specifically detects an abundant 1.5 kb RNA in the placental RNA preparation (position indicated by arrow). A faint band of similar size if also observed in liver RNA. Numbers at the left indicate positions and sizes (in kb) of RNA markers.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

DNA segment. A DNA segment, as is generally understood and used herein, refers to a molecule comprising a linear stretch of nucleotides wherein the nucleotides are present in a sequence that may encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

A "complementary DNA" or "cDNA" gene includes recombinant genes synthesized by reverse transcription of messenger RNA ("mRNA").

Structural gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome may be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA may be inserted to be cloned. The vector may replicate autonomously in a host cell, and may be further characterized by one or a small number of endonuclease recognition sites at which such DNA sequences may be cut in a determinable fashion and into which DNA may be inserted. The vector may further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art.

Fragment. A "fragment" of a molecule such as a protein or nucleic acid is meant to refer to any portion of the amino acid or nucleotide genetic sequence.

Variant. A "variant" of a protein or nucleic acid is meant to refer to a molecule substantially similar in structure and biological activity to either a the protein or nucleic acid, or to a fragment thereof. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Analog. An "analog" of a protein or genetic sequence is meant to refer to a protein or genetic sequence substantially similar in function to a protein or genetic sequence described herein.

Allele. An "allele" is an alternative form of a gene occupying a given locus on the chromosome.

Mutation. A "mutation" is any detectable change in the genetic material which may be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells. A mutation may be any (or a combination of) detectable, unnatural change affecting the chemical or physical constitution, mutability, replication, phenotypic function, or recombination of one or more deoxyribonucleotides; nucleotides may be added, deleted, substituted for, inverted, or transposed to new positions with and without inversion. Mutations may occur spontaneously and can be induced experimentally by application of mutagens. A mutant variation of a DNA segment results from a mutation. A mutant polypeptide may result from a mutant DNA segment.

Species. A "species" is a group of actually or potentially interbreeding natural populations. A species variation within a DNA segment or protein is a change in the nucleic acid or amino acid sequence that occurs among species and may be determined by DNA sequencing of the segment in question.

Substantially Pure. A "substantially pure" protein or nucleic acid is a protein or nucleic acid preparation that is generally lacking in other cellular components.

DETAILED DESCRIPTION OF THE INVENTION

The present invention relates to novel DNA sequences, EBI 1, EBI 2, and EBI 3, which have been identified as Epstein Barr virus induced genes.

A. DNA Segments Coding for EBI 1, EBI 2, and EBI 3 Polypeptides, and Fragments Thereof In one embodiment, the present invention relates to a DNA segment coding for a polypeptide having an amino acid sequence corresponding to a polypeptide selected from the group consisting of EBI 1, EBI 2, and EBI 3 polypeptides, or at least 7 contiguous amino acids thereof (preferably, at least 10, 15, 20, or 30 contiguous amino acids thereof). In one preferred embodiment, the DNA segment comprises the sequences set forth in SEQ ID NO: 1, SEQ ID NO:3, or SEQ ID NO:5; allelic, mutant or species variation thereof, or at least 20 contiguous nucleotides thereof (preferably at least 25, 30, 40, or 50 contiguous nucleotides thereof). In another preferred embodiment, the DNA segment encodes an amino acid sequence selected from the group consisting of sequences set forth in SEQ ID NO:2, SEQ ID NO:4, and SEQ ID NO:6, or mutant or species variation thereof, or at least 7 contiguous amino acids thereof (preferably, at least 10, 15, 20, or 30 contiguous amino acids thereof).

Also included within the scope of this invention are the functional equivalents of the herein-described DNA or nucleotide sequences. The degeneracy of the genetic code permits substitution of certain codons by other codons which specify the same amino acid and hence would give rise to the same protein. The DNA or nucleotide sequence can vary substantially since, with the exception of methionine and tryptophan, the known amino acids can be coded for by more than one codon. Thus, portions or all of the EBI 1, EBI 2, or EBI 3 gene could be synthesized to give a DNA sequence significantly different from that shown in SEQ ID NO: 1, SEQ ID NO:3, or SEQ ID NO:5. The encoded amino acid sequence thereof would, however, be preserved.

In addition, the DNA or nucleotide sequence may comprise a nucleotide sequence which results from the addition, deletion or substitution of at least one nucleotide to the 5'-end and/or the 3'-end of the DNA formula shown in SEQ ID NO:1, SEQ ID NO:3, or SEQ ID NO:5 or a derivative thereof. Any nucleotide or polynucleotide may be used in this regard, provided that its addition, deletion or substitution does not alter the amino acid sequence of SEQ ID NO:2, SEQ ID NO:4, or SEQ ID NO:6 which is encoded by the nucleotide sequence. For example, the present invention is intended to include any nucleotide sequence resulting from the addition of ATG as an initiation codon at the 5'-end of the inventive nucleotide sequence or its derivative, or from the addition of TTA, TAG or TGA as a termination codon at the 3'-end of the inventive nucleotide sequence or its derivative. Moreover, the DNA fragment of the present invention may, as necessary, have restriction endonuclease recognition sites added to its 5'-end and/or 3'-end.

Such functional alterations of a given DNA or nucleotide sequence afford an opportunity to promote secretion and/or processing of heterologous proteins encoded by foreign DNA sequences fused thereto. All variations of the nucleotide sequence of the EBI 1, EBI 2, and EBI 3 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified DNA molecule. As recognized in the art, the two polypeptides are functionally equivalent, as are the two DNA molecules which give rise to their production, even though the differences between the DNA molecules are not related to degeneracy of the genetic code.

A.1. Isolation of DNA.

In one aspect of the present invention, DNA segments coding for polypeptides having amino acid sequences corresponding to EBI 1, EBI 2, and EBI 3 are provided. In particular, the DNA segment may be isolated from a biological sample containing RNA or DNA.

The DNA segment may be isolated from a biological sample containing RNA using the techniques of cDNA cloning and subtractive hybridization as previously described (Birkenbach et al., *J. of Virology* 63:9:4079–4084). The DNA segment may also be isolated from a cDNA library using a homologous probe.

The DNA segment may be isolated from a biological sample containing Genoa DNA or from a Genoa library using techniques well known in the art. Suitable biological samples include, but are not limited to, blood, semen and tissue. The method of obtaining the biological sample will vary depending upon the nature of the sample.

One skilled in the art will realize that the human genome may be subject to slight allelic variations between individuals. Therefore, the isolated DNA segment is also intended to include allelic variations, so long as the sequence is a functional derivative of the EBI 1, EBI 2, or EBI 3 gene.

One skilled in the art will realize that organisms other than humans may also contain EBI 1, EBI 2, or EBI 3 genes (for example, eukaryotes; more specifically, mammals, birds, fish, and plants; more specifically, gorillas, rhesus monkeys, and chimpanzees). The invention is intended to include, but not be limited to, EBI 1, EBI 2, and EBI 3 DNA segments isolated from the above-described organisms.

A.2. Synthesis of DNA.

In the alternative, the DNA segment of the present invention may be chemically synthesized. For example, a DNA fragment with the nucleotide sequence which codes for the expression product of an EBI 1, EBI 2, or EBI 3 gene may be designed and, if necessary, divided into appropriate smaller fragments. Then an oligomer which corresponds to the DNA fragment, or to each of the divided fragments, may be synthesized. Such synthetic oligonucleotides may be prepared, for example, by the triester method of Matteucci et al., *J. Am. Chem. Soc.* 103:3185–3191 (1981) or by using an automated DNA synthesizer.

An oligonucleotide may be derived synthetically or by cloning. If necessary, the 5'-ends of the oligomers may be phosphorylated using T4 polynucleotide kinase. Kinasing of single strands prior to annealing or for labeling may be achieved using an excess of the enzyme. If kinasing is for the labeling of probe, the ATP may contain high specific activity radioisotopes. Then, the DNA oligomer may be subjected to annealing and ligation with T4 ligase or the like.

B. A Substantially Pure EBI 1, EBI 2, and EBI 3 Polypeptides.

In another embodiment, the present invention relates to a substantially pure polypeptide having an amino acid sequence corresponding to a polypeptide selected from the group consisting of EBI 1, EBI 2, and EBI 3 polypeptides, or at least 7 contiguous amino acids thereof (preferably, at least 10, 15, 20, or 30 contiguous amino acids thereof). In a preferred embodiment, the polypeptide has an amino acid sequence selected from the group consisting of sequences set forth in SEQ ID NO:2, SEQ ID NO:4, and SEQ ID NO:6, or mutant or species variation thereof, or at least 7 contiguous amino acids thereof (preferably, at least 10, 15, 20, or 30 contiguous amino acids thereof).

A variety of methodologies known in the art can be utilized to obtain the peptide of the present invention. In one embodiment, the peptide is purified from tissues or cells which naturally produce the peptide. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromotography, size-exclusion chromatography, HPLC, ion-exchange chromatography, and immuno-affinity chromatography.

C. A Nucleic Acid Probe for the Detection of Epstein Barr Virus.

In another embodiment, the present invention relates to a nucleic acid probe for the detection of the presence of Epstein Barr Virus in a sample comprising the above-described DNA segments or at least 20 contiguous nucleotides thereof (preferably at least 25, 30, 40, or 50 thereof). In another preferred embodiment, the DNA segment has a nucleic acid sequence selected from the group consisting of sequences set forth in SEQ ID NO: 1, SEQ ID NO:3, and SEQ ID NO:5, or at least 20 contiguous nucleotides thereof (preferably at least 25, 30, 40, or 50 thereof). In another preferred embodiment, the nucleic acid probe encodes an amino acid sequence selected from the group consisting of sequences set forth in SEQ ID NO:2, SEQ ID NO:4, and SEQ ID NO:6, or at least 7 contiguous amino acids thereof.

The nucleic acid probe may be used to probe an appropriate chromosomal or cDNA library by usual hybridization methods to obtain another DNA segment of the present invention. A chromosomal DNA or cDNA library may be prepared from appropriate cells according to recognized methods in the art (cf. *Molecular Cloning: A Laboratory Manual*, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to *PCR Protocols, A Guide to Methods and Applications*, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. *Molecular Cloning: A Laboratory Manual*, second edition, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

D. A Method of Detecting the Presence of Epstein Barr Virus in a Sample.

In another embodiment, the present invention relates to a method of detecting the presence of Epstein Barr virus in a sample comprising a) contacting said sample with the above-described nucleic acid probe, under conditions such that hybridization occurs, and b) detecting the presence of said probe bound to said DNA segment. One skilled in the art would select the nucleic acid probe according to techniques known in the art as described above. Samples to be tested include but should not be limited to RNA samples of human tissue. The presence of EBI 1, EBI 2, or EBI 3 may represent that the cells had been infected with the Epstein Barr virus. Increases in the amount of EBI 1, EBI 2, or EBI 3 RNA in a sample may also indicate the presence of or infection with the Epstein Barr virus.

E. A Kit For Detecting the Presence of Epstein Barr Virus in a Sample.

In another embodiment, the present invention relates to a kit for detecting the presence of Epstein Barr virus in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

F. DNA Constructs Comprising the EBI 1, EBI 2, or EBI 3 DNA Segments and Cells Containing these Constructs.

In another embodiment, the present invention relates to a recombinant DNA molecule comprising, 5' to 3', a promoter effective to initiate transcription in a host cell and the above-described DNA segments.

In another embodiment, the present invention relates to a recombinant DNA molecule comprising a vector and an above-described DNA segment.

In another embodiment, the present invention relates to a DNA molecule comprising a transcriptional region functional in a cell, a sequence complimentary to an RNA sequence encoding an amino acid sequence corresponding to the above-described polypeptide, and a transcriptional termination region functional in said cell.

Preferably, the above-described molecules are isolated and/or purified DNA molecules.

In another embodiment, the present invention relates to a cell that contains an above-described DNA molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with- initiation of transcription and translation, such as the TATA box, capping sequence, CAAT sequence, and the like.

If desired, the non-coding region 3' to the sequence encoding an EBI 1, EBI 2, or EBI 3 gene may be obtained by the above-described methods. This region may be retained for its transcriptional termination regulatory sequences, such as termination and polyadenylation. Thus, by retaining the 3'-region naturally contiguous to the DNA sequence encoding an EBI 1, EBI 2, or EBI 3 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an EBI 1, EBI 2, or EBI 3 sequence) are said to be operably linked if the nature of the linkage between the two DNA sequences does not (1) result in the introduction of a frame-shift mutation, (2) interfere with the ability of the promoter region sequence to direct the transcription of an EBI 1, EBI 2, EBI 3 gene sequence, or (3) interfere with the ability of the an EBI 1, EBI 2, or EBI 3 gene sequence to be transcribed by the promoter region sequence. Thus, a promoter region would be operably linked to a DNA sequence if the promoter were capable of effecting transcription of that DNA sequence.

Thus, to express an EBI 1, EBI 2, or EBI 3 gene, transcriptional and translational signals recognized by an appropriate host are necessary.

The present invention encompasses the expression of the EBI 1, EBI 2, or EBI 3 gene (or a functional derivative thereof) in either prokaryotic or eukaryotic cells. Prokaryotic hosts are, generally, the most efficient and convenient for the production of recombinant proteins and, therefore, are preferred for the expression of the EBI 1, EBI 2, or EBI 3 gene.

Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC18, pUC19 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express EBI 1, 2, or 3 (or a functional derivative thereof) in a prokaryotic cell, it is necessary to operably link the EBI 1, EBI 2, or EBI 3 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of Bacillus (Gryczan, In: *The Molecular Biology of the*

*Bacilli*, Academic Press, Inc., NY (1982)), and Streptomyces promoters (Ward et al., *Mol. Gen. Genet.* 203:468–478 (1986)).

Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the EBI 1, 2, or 3 peptide of interest. Suitable hosts may often include eukaryotic cells.

Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin, such as the hybridoma SP2/O-AG14 or the myeloma P3x63Sg8, and their derivatives. Preferred mammalian host cells include SP2/0 and J558L, as well as neuroblastoma cell lines such as IMR 332 that may provide better capacities for correct post-translational processing.

In addition, plant cells are also available as hosts, and control sequences compatible with plant cells are available, such as the nopaline synthase promoter and polyadenylation signal sequences.

Another preferred host is an insect cell, for example the Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of EBI 1, EBI 2, or EBI 3 in insects cells (Jasny, *Science* 238:1653 (1987); Miller et al., In: *Genetic Engineering* (1986), Setlow, J. K., et al., eds., *Plenum*, Vol. 8, pp. 277–291).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glyco-lytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of EBI 1, EBI 2, or EBI 3.

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of EBI 1, EBI 2, or EBI 3 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci.* (*USA*) 79:6971–6975 (1982); Silver et al., *Proc. Natl. Acad. Sci.* (*USA*) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes EBI 1, EBI 2, or EBI 3 (or a functional derivative thereof) does not contain any intervening codons which are capable of encoding a methionine (i.e., AUG). The presence of such codons results either in a formation of a fusion protein (if the AUG codon is in the same reading frame as the EBI 1, EBI 2, or EBI 3 coding sequence) or a frame-shift mutation (if the AUG codon is not in the same reading frame as the EBI 1, EBI 2, or EBI 3 coding sequence).

An EBI 1, EBI 2, or EBI 3 DNA segment and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA.

These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989)). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (Jpn. *J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)).

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. After the introduction of the vector, recipient cells are grown in a selective medium, which selects for the growth of vector-containing cells. Expression of the cloned gene sequencers) results in the production of EBI 1, EBI 2, or EBI 3, or fragments thereof. This can take place in the transformed cells as such, or following the induction of these cells to differentiate (for example, by administration of bromodeoxyuracil to neuroblastoma cells or the like).

A variety of incubation conditions can be used to form the peptide of the present invention. The most preferred conditions are those which mimic physiological conditions.

G. An Antibody Having Binding Affinity to an EBI 1, EBI 2, and EBI 3 Polypeptide, or a Binding Fragment thereof and a Hybridoma Containing the Antibody.

In another embodiment, the present invention relates to an antibody having binding affinity to a polypeptide having an amino acid sequence selected from the group consisting of EBI 1, EBI 2, and EBI 3 polypeptides, or a binding fragment thereof. In a preferred embodiment, the polypeptide has an amino acid sequence selected from the group of sequences set forth in SEQ ID NO:2, SEQ ID NO:4, and SEQ ID NO:6, or mutant or species variation thereof, or at least 7 contiguous amino acids thereof (preferably, at least 10, 15, 20, or 30 contiguous amino acids thereof). In another preferred embodiment, the antibody is a monoclonal antibody.

In another embodiment, the present invention relates to a hybridoma which produces the above-described monoclonal antibody, or binding fragment thereof.

The EBI 1, EBI 2, or EBI 3 proteins of the present invention can be used in a variety of procedures and methods, such as for the generation of antibodies, for use in identifying pharmaceutical compositions, and for studying DNA/protein interaction.

The EBI 1, EBI 2, or EBI 3 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

The invention also provides hybridomas which are capable of producing the above-described antibodies. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or 62-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., *"Handbook of Experimental Immunology"* 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, NY, pp. 289–307 (1992), and Kaspczak et al., *Biochemistry* 28:9230–8 (1989).

Anti-peptide peptides can be generated in one: of two fashions. First, the anti-peptide peptides can be generated by replacing the basic amino acid residues found in the EBI 1, EBI 2, or EBI 3 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

H. A Method of Detecting an EBI 1, EBI 2, or EBI 3 Polypeptide in a Sample.

In another embodiment, the present invention relates to a method of detecting a polypeptide selected from the group consisting of EBI 1, EBI 2, EBI 3 in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. The presence of an EBI 1, EBI 2, or EBI 3 polypeptide or fragment thereof in a sample may indicate the presence or infection of Epstein Barr virus.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *"An Introduction to Radioimmunoassay and Related Techniques"* Elsevier Science Publishers, Amsterdam, The Netherlands (1986); Bullock et al., *"Techniques in Immunocytochemistry,"* Academic Press, Orlando, Fla. Vol. 1 (1982), Vol. 2 (1983), Vol. 3 (1985); Tijssen, *"Practice and Theory of Enzyme Immunoassays: Laboratory Techniques in Biochemistry and Molecular Biology,"* Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

I. A Diagnostic Kit Comprising Antibodies to EBI 1, EBI 2, and EBI 3

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits.

One skilled in the art will readily recognize that the antibodies described in the present invention can readily be incorporated into one of the established kit formats which are well known in the art.

The present invention is described in further detail in the following non-limiting examples.

EXAMPLES

The following protocols and experimental details are referenced in the examples that follow:

Cells and cell lines. BL41 and BL30 are EBV(−) Burkitt lymphoma cell lines. The BL41I/B95-8 and BL41/P3HR1 cell lines were derived by infecting BL41 with the transforming EBV strain, B95-8, or with the non-transforming strain, P3HR1, respectively (Favrot, M. C., et al., *Intl. J.*

Cancer 38(6):901–6 (1986)). IB4 is a latently infected B lymphoblastoid cell line established by infection of B lymphocytes with EBV (B95-8) in vitro. RHEK-1 (generous gift from Dr. Jong Rhim, National Cancer Institute, Bethesda, Mass.) is a human keratinocyte line derived by infection of primary foreskin epithelial cells with an adenovirus 12/SV40 hybrid-virus. K562 is a Philadelphia chromosome-positive human chronic myeloid leukemia cell line. U937 is a histiocytic lymphoma cell line with monocytic features. HL60 is a promyelocytic leukemia line. HSB-2 and Jurkat are human T lymphoblastic leukemia cell lines. TK143 was derived from a human osteosarcoma.

Human mononuclear cells (PBMC) were purified from peripheral blood by centrifugation on a ficoll cushion (Ficoll-Hypague, Pharmacia, Vineland, N.J.). Cells were resuspended at $1\times10^6$ cells/ml in RPMI medium supplemented with 20% fetal bovine serum, and were divided into parallel cultures grown 72 h with or without 2.5 μg/ml pokeweed mitogen (PWM, Sigma, St. Louis, Mo.). T cells were isolated from purified PBMCs by rosetting overnight with aminoethylisothiouronium bromide (AET) treated sheep erythrocytes at 4° C., followed by centrifugation over ficoll. Pelleted erythrocytes were lysed with ammonium chloride. The remaining T cells were resuspended in RPMI with 20% fetal bovine serum at $1\times10^6$ cells/ml. Phytohemagglutinin (PHA, Sigma) was added to a final concentration of 1.0 μg/ml. Cells were cultured for 72 h and harvested for extraction of total cellular RNA.

RNA preparation and analysis. Cytoplasmic RNA was isolated from exponentially growing cells by a modification of the acid phenol/guanidinium isothiocyanate extraction procedure, followed by reprecipitation in guanidinium hydrochloride/ethanol. Total cellular RNA was extracted from 0.2 to 2 g samples of human spleen and tonsil obtained from surgical specimens, and from human postmortem bone marrow. Tissues were homogenized in acid phenol/guanidinium isothiocyanate using a rotary tissue homogenizer, extracted and precipitated. After dissolution in guanidinium hydrochloride and reprecipitation with ethanol, human tissue RNA samples were resuspended in $H_2O$ and precipitated by addition of an equal volume of 8 M LiCl. The polyadenylated fractions of BL41 or BL41/B95-8 RNA were purified by 2 successive cycles of chromatography on oligodeoxythymidylate cellulose. Polyadenylated IB4 RNA was purified by a single round of oligodeoxythymidylate selection. RNA samples (12 μg per lane) were size fractionated on 0.66 M formaldehyde, 1% agarose gels and transferred to charged nylon membranes (GeneScreen Plus, New England Nuclear, Billerica, Mass.) for subsequent hybridization analysis. To examine gene expression in other human tissues, a commercially prepared blot was purchased containing 2 μg of polyadenylated heart, brain, placenta, lung, liver, kidney, skeletal muscle and pancreas RNA (Multiple Tissue Northern, Clontech, Palo Alto, Calif.).

Probes were prepared from cloned cDNA inserts using random hexamer primers and $^{32}$P-dCTP. The beta actin probe was generated using apreviously described 1.4 kb cDNA (Alfieri, C., et al., Virology 181(2):595–608 (1991)). The glyceraldehyde phosphate dehydrogenase (GAPDH) probe was prepared from a commercially obtained DNA fragment (Clontech). Filters were hybridized for 18 to 24 h at 47° C. in a hybridization buffer consisting of 50% formamide, 6×SSPE (20×SSPE: 3.0 M NaCl, 200 mM NaPO4, pH7.4, 20 mM EDTA), 1% SDS, 1×Denhardt's solution (100×Denhardt's: 2% BSA, 2% polyvinylpyrrolidone, 2% Ficoll), and 100 μg/ml sheared single-stranded herring testis DNA. Filters were washed according to the manufacturers' instructions, with high stringency washes performed at 67–70° C. in 1% SDS, 0.2×SSC, and exposed to preflashed film (X-OMAT AR, Kodak, Rochester, N.Y.) at −80° C. for 2 h to 10 days. Autoradiographic signal intensities were quantitated by densitometric scanning using a Beckman DU-8 spectrophotometer equipped with a slab gel Compuset Module. Induction factors were calculated for each probe as signal intensity ratios for EBV(+) versus EBV(−) cells, divided by the ratio of beta actin signal intensities.

cDNA library preparation. First strand cDNA was prepared from 5 μg polyadenylylated BL41/B95-8 RNA using Moloney murine leukemia virus reverse transcriptase (SuperScript, Bethesda Research Laboratories, Gaithersburg, Md.) and oligodeoxthymidylate primers in a 100 μL reaction. Second strand cDNA was synthesized using E. coli DNA polymerase I and RNAse H. The double stranded cDNA was blunt-ended with T4 DNA polymerase and EcoRI methylated. After ligation of EcoRI linkers, the cDNA was EcoRI restriction digested and size fractionated by gel filtration chromatography on Sepharose CL-4B. The purified cDNA was ligated to phosphorylated lambda gt10 arms (Promega, Madison, Wis. and packaged (Gigapack Gold, Stratagene, La Jolla, Calif.).

Subtractive probe preparation. Radiolabelled cDNA was prepared from 6 μg of polyadenylylated BL41 or BL41/B95-8 RNA in a 200 μL reaction containing 50 μg/ml random DNA hexamers; 0.5 mM dATP, dGTP, dTTP; 25 μM unlabelled dCTP; 1.0 mCi $^{32}$P-dCTP (800 Ci/mMole, New England Nuclear); 2000 units recombinant Moloney murine leukemia virus reverse transcriptase. Reactions were 42° C. for 1 h. After precipitation, reaction products were resuspended in 0.1 M NaOH and incubated 20 min. at 65° C. to hydrolyze RNA templates. Probes were neutralized with 0.1 M acetic acid and size fractionated on G-50 Sephadex. Biotinylated RNA was prepared from polyadenylylated BL41 RNA using a photoactivatable azido-aryl biotin reagent (Photoprobe Biotin, Vector Laboratories, Burlingame, Calif.) following the manufacturer's protocol. Probe fractions were combined with 48 μg (for BL41/B95-8 probe) or 12 μg (for BL41 probe) biotinylated BL41 RNA and precipitated with ethanol. BL41/B95-8 probes were hybridized with an 8 fold excess (2 mg/ml) of biotinylated BL41 RNA; while BL41 control probes were hybridized with a 2 fold excess (0.5 μg/ml) of biotinylated BL41 RNA. Hybridizations and subtractions were performed using the "Subtractor" kit (Invitrogen, San Diego, Calif.) according to the manufacturer's instructions. The precipitated cDNA/RNA mixtures were resuspended in 10 to 20 μL $H_2O$ and heated to 100° C. for 1 min. An equal volume of 2×hybridization buffer (Invitrogen) was added and the mixture was incubated at 65° C. for 20 to 24 h. Following addition of an equal volume of HEPES buffer (10 mM HEPES, pH 7.5, 1 mM EDTA), 20 μg streptavidin was added and the mixture was incubated on ice for 10 min. Biotinylated RNA and RNA:cDNA duplexes, complexed with avidin, were removed by repeated phenol/chloroform extractions. The single stranded, subtracted BL41 cDNA probe which remained in the aqueous phase was used directly for in situ filter hybridizations. Aqueous phase BL41/B95-8 cDNA probe was precipitated with ethanol and subjected to a second round of subtraction under identical conditions prior to use in filter hybridizations. Duplicate filters were made from 145 mm plates containing 6000 recombinant bacteriophage and were hybridized in parallel to equal amounts of BL41/B95-8 or BL41 subtracted probes. Filters were hybridized at 48° C. for 48 to 72 h in a buffer consisting of 50% formamide, 6×SSPE, 1% SDS, 10% dextran sulfate, 2×Denhardt's solution, 100 μg/ml sheared single-stranded herring testis DNA, and 10 μg/ml poly rA:rU (Sigma, St. Louis, Mo.). Filters were washed at 72° C. in 0.2×SSC and exposed 3 to 7 days to preflashed film (Kodak X-OMAT AR). Differentially expressed genes were identified by overlaying films from corresponding filters. Clones selected on primary screening were rescreened once at low density to verify differential expression and for plaque purification.

Analysis of clones. DNA was extracted from bulk liquid cultures of purified lambda gt10 clones and digested with EcoRI. cDNA inserts were purified by agarose gel electrophoresis and subcloned into pBluescript (+). Nucleotide sequences were determined and were compared by the BLAST algorithm (Altschul, S.F., et al., *J. Mol. Biol.* 215 (3):403–10 (1990)) with known sequences resident in the National Center for Biotechnology Information databases using the Experimental GENINFO® BLAST Network Service, accessed through the Molecular Biology Computer Research Resource of the Dana-Farber Cancer Institute. Multiple sequence alignments were performed by the method of Higgins and Sharp (Higgins and Sharp, *Gene* 73(1):237–44 (1988)) using the CLUSTAL program (PCGene, IntelliGenetics, Mountain View, Calif.) with open gap and unit gap costs of 10.

EXAMPLE 1

Identification of cDNA Clones of EBV Induced RNAs by Subtracted Probe Hybridization CDNA clones of RNA from an in vitro EBV-infected BL cell line, BL41I/B95-8 [EBV(+) BL41], were differentially screened with an EBV(+) BL41 cDNA probe from which sequences complementary to EBV(-) BL41 cell RNA had been specifically removed, and with an EBV(-) BL41 control cDNA probe. Sequences complimentary to EBV(-) BL41 RNA were removed from the EBV(+) BL41 RNA cDNA probes by two subtractions with an 8 fold excess of biotinylated EBV(-) BL41 RNA. Overall, 85–95% of the labeled EBV(+) BL41 probe was removed by the two subtractions. EBV(-) BL41 cDNA control probe was subtracted only once, removing 60–85% of the probe; thereby reducing hybridization to plaques containing cDNAs from abundant RNAs so that hybridization to cDNAs from less abundant BL41 RNAs was evident.

Seventy-five phage cDNA clones differentially hybridized to the EBV(+) BL41 probe on the first screen of 75,000 recombinant phage. Twenty-five clones were consistently positive on rescreening. The eighteen clones which demonstrated the greatest reactivity with the EBV(+) versus the EBV(-) BL41 cDNA probes were selected for nucleotide sequencing and RNA blot hybridization.

EXAMPLE 2

Nucleotide Sequences of EBV Induced cDNAs

The first 12 clones are described in Table 1. Ten clones matched 7 previously characterized genes: two independent clones each of the complement receptor type 2 (CD21), the serglycin proteoglycan core protein and vimentin; and one clone each of cathepsin H, annexin VI (p68), the myristylated alanine-rich protein kinase C substrate (MARCKS) and the lymphocyte hyaluronic acid receptor (CD44). The 2.6 kb MARCKS cDNA precisely matched the previous 1.58 kb human MARCKS cDNA clone (Harlan, D. M., et al., *J. Biol. Chem.* 266(22):14399–405 (1991)) at its 5 prime end. The 3 prime untranslated region of the new clone is highly homologous to bovine MARCKS cDNA (Stumpo, D. J., et al., *Proc. Natl. Acad. Sci. USA* 86(11):4012–6 (1989)).

The two remaining clones are from novel RNAs, EBV induced genes 1 (EBI 1) and 2 (EBI 2), whose nucleotide sequences can be predicted to encode G-protein coupled peptide receptors. The complete nucleotide and deduced amino acid sequences of the EBI 1 and EBI 2 cDNAs are shown in FIGS. 1A and 1B, respectively. Because the first EBI 1 cDNA was 1.2 kb, significantly shorter than the 2.4 kb RNA, 20 other cDNA clones were obtained using the initial cDNA as a probe. The largest clone is 2153 nucleotides (nt) and has a 1134 nt open-reading frame (FIG. 1A). This clone is probably nearly full length, since it is close to the expected size, considering it has only a short poly A tail. Translation is likely to initiate from either of two AUGs, at nt 64–66 or 82–84, the first of which conforms to a consensus translational initiation sequence (Kozak, M., *J. Biol. Chem.* 266 (30): 19867–70 (1991)). An in-frame stop codon at nt 10–12 is consistent with downstream initiation at nt 64–66. The polypeptide encoded by the sequence beginning at nt 64 has a predicted molecular weight of 42.7 kD and includes eight hydrophobic domains likely to mediate membrane insertion. The first hydrophobic domain begins at the amino terminus and ends at a predicted signal peptidase cleavage site. The 7 remaining hydrophobic domains are characteristic of the G-protein coupled receptor family. Potential asparagine linked glycosylation sites are present in the extracellular amino terminal segment and in the third extracellular loop.

Since the initial EBI 2 cDNA was 1643 nt and approximated the size expected from a 1.9kb polyadenylated RNA, further cDNA clones were not obtained. The EBI 2 cDNA contains a 1083 nt open reading frame with two methionine codons are at nt 34–36 and 46–48 (FIG. 1B). Although neither methionine codon is in a favored initiation context (Kozak, M., *J. Biol. Chem.* 266(30):19867–70 (1991)), an upstream, in-frame termination codon and the absence of other potential open reading frames is consistent with translation initiating at the first or second methionine codon. Initiation at the first would result in a 41.2 kD protein. The deduced amino acid sequence predicts 7 hydrophobic transmembrane segments in the characteristic configuration of G-protein coupled receptors. In contrast to the EBI 1 protein, EBI 2 lacks a signal peptide. A possible N-linked glycosylation site is found in the amino terminal extracellular domain. Though the EBI 2 cDNA lacks a polyadenylate tail, a canonical polyadenylation signal (AATAAA) near the 3 prime end is consistent with the cDNA being essentially complete.

EXAMPLE 3

Comparison of EBI 1 and 2 with other G Protein Coupled Receptors

The EBI 1 and EBI 2 nucleotide and predicted amino acid sequences were compared with the Genbank (release 72 and updates), EMBL (release 31), Genbank translation, Swiss protein (release 22) and Protein Identification Resource (PIR, release 33) databases, using the BLAST algorithm (Altschul, S. F., et al., *J. Mol. Biol.* 215(3):403–10 (1990)). EBI 1 and EBI 2 are homologous to G protein associated receptors. EBI 1 is highly homologous to the human high or low affinity interleukin 8 (IL-8) receptors at both the nucleotide (data not shown) and amino acid sequence levels. IL8 receptor itself is not expressed on lymphocytes (Holmes, W. E., et al., *Science* 253(5025):1278–80 (1991); Murphy and Tiffany, et al., Science 253:1280–1283 (1991)). Excluding the putative EBI 1 signal peptide, the overall amino acid identity among the 3 proteins exceeds 30%, with conservative changes observed at many of the non-identical residues. The identity increases to 40% when EBI 1 is compared with either IL-8 receptor individually. Additional similarities with the IL-8 receptors include a high proportion of serine and threonine near the carboxy terminus, and a highly acidic amino terminal extracellular domain. The IL-8 receptor acidic residues are implicated in binding IL-8 basic amino acids (Holmes, W. E., et al., Science 253(5025):1278–80 (1991); Murphy and Tiffany, etal., Science 253:1280–1283 (1991).

The EBI 2 gene does not have such a close homologue. EBI 2 has 24% amino acid identity to the thrombin receptor (Vu, T. K., et al., Cell 64(6):1057–68 (1991)). Less extensive homologies are observed with a number of other G-protein coupled receptors, including the receptors for vasoactive intestinal polypeptide, somatostatin (type 1) and angiotensin II, as well as the low affinity IL-8 receptor. EBI 2 also exhibits more distant homologies with EBI 1 and the high affinity IL-8 receptor. Significantly, these are the same proteins which, in different order, exhibit the closest homologies with the EBI 1 protein. Together they constitute a subfamily of G-protein coupled peptide receptors. The greatest conservation of residues among these proteins extends from the first transmembrane domain to the second intracellular loop. Because of the particular conservation of an amino acid sequence among these G protein coupled receptors, we are able to identify a new highly conserved sequence motif at the carboxy end of TM III and the adjacent second intracellular loop. This motif, S-(I/L)-D-R-(Y/F)-X-X-X-X, with x being a hydrophobic amino acid, is in a wide variety of G-protein coupled receptors; and is not in other proteins in the data bases surveyed. Other highly conserved features of G protein coupled receptors in EBI 1 and 2 include the asparagine in TM I, the proline in TM II, the aspartate in the first intracellular loop, and the tryptophane and cysteine in the first extracellular loop. This cysteine has been postulated to be involved in disulfide linkage to a conserved cysteine present in the second extracellular loop in several other receptors, including the beta adrenergic and thrombin receptors.

EXAMPLE 4

Analysis of Induced Gene Expression by RNA Blot Hybridization

Probes from seven of the nine EBV induced cDNAs were hybridized to identical blots of polyadenylated RNA from the EBV(+) or EBV(−) BL41 cell lines or from the EBV transformed lymphoblastoid cell line, IB4 (FIG. 2). Vimentin and CD21 were previously shown to be EBV induced and were not further evaluated. The RNAs loaded in the EBV(+), BL41, and EBV(−) BL41 lanes were standardized with respect to beta actin reactivity. Significantly less IB4 cell RNA was used due to the high abundance of the putative induced gene RNAs in these cells (FIG. 2, Actin probe). Probes from each of the cDNA clones detected RNAs which are significantly more abundant in both IB4 and EBV(+) BL41 cells than in EBV(−) BL41 cells. Induction factors indicated in Table 1 were determined by quantitative densitometric scanning of autoradiographs and reflect the fold enhancement of signal intensities in EBV(+) BL41 cells compared with EBV(−) BL41 cells, corrected for the ratio of actin reactivities. Standardization by actin reactivity, however, significantly underestimates the absolute induction levels since actin is induced 3-fold by EBV infection of BL41 cells relative to glyceraldehyde phosphate dehydrogenase, (GAPDH), or to total RNA amounts quantitated spectrophotmetrically. To achieve equal actin signal intensities, 3-fold more EBV(−) BL41 than EBV(+) BL41 RNA was loaded per lane. Importantly, each of the RNAs was at least as abundant in IB4 cells relative to GADPH as in EBV(+) BL41 (FIG. 2).

EBI 1, EBI 2, CD44 and MARCKS are the most induced of the seven genes. The CD44 gene encodes three distinct RNAs of 1.6, 2.2 and 4.8 kb respectively in both IB4 and EBV(+) BL41 cells. No CD44 RNA was detected EBV(−) BL41 cells even after prolonged autoradiographic exposures. EBI 2 RNA was also undetectable in EBV(−) BL41 cells.

EXAMPLE 5

Expression of ESI 1 and 2 in Human Cell Lines and Tissues

Figure 3:
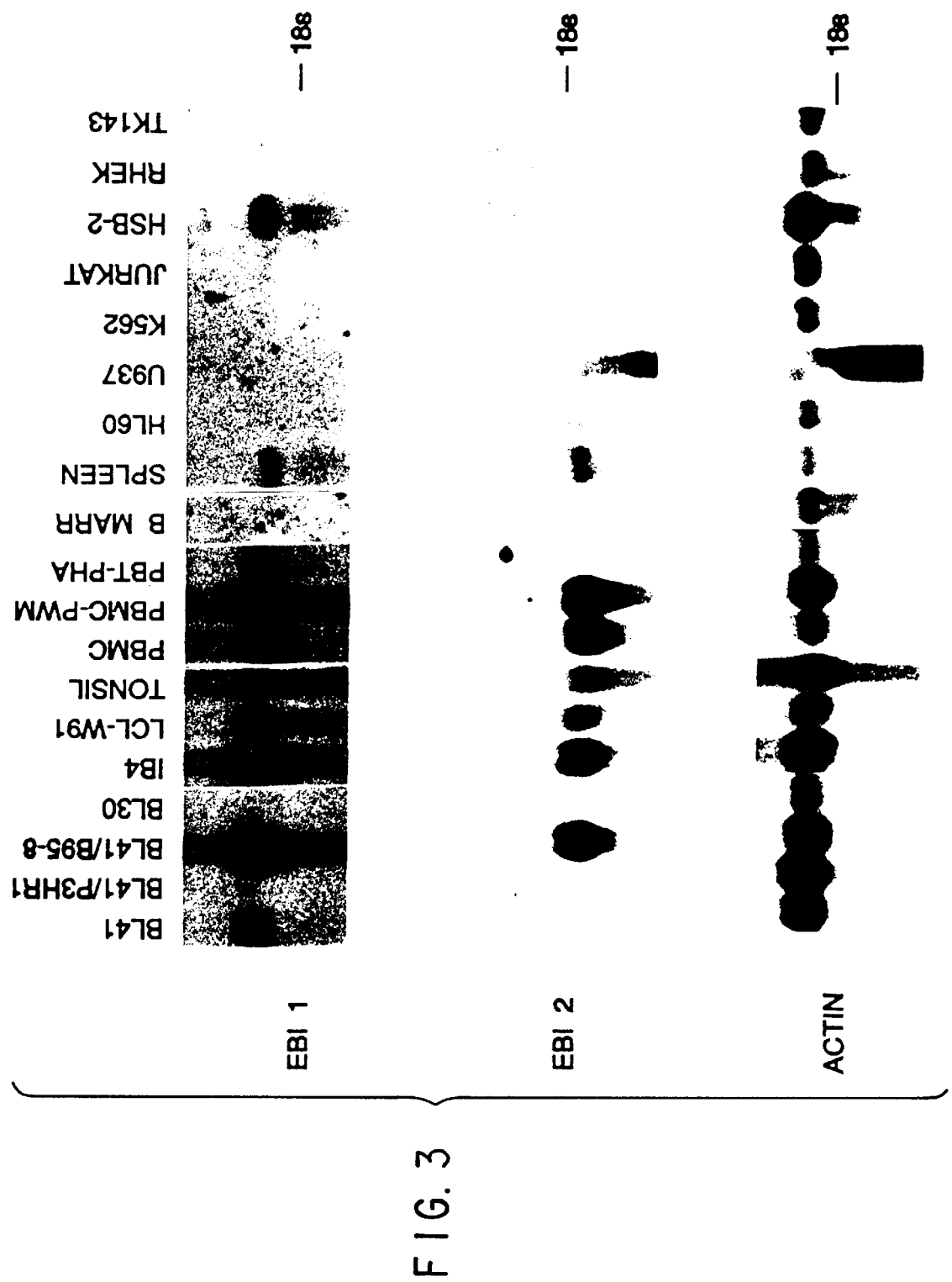

The expression of EBI 1 and 2 in human cell lines and tissues was evaluated by hybridizing actin, EBI 1 or EBI 2 probes to blots of cell line or tissue RNAs. While EBI 1 is weakly expressed in BL41, EBI 2 is not; and, neither EBI 1 nor EBI 2 are expressed in another EBV(−) BL cell line, BL30 (FIG. 3). EBI 1 and EBI 2 RNAs are abundant in primary human lymphocytes transformed by EBV in vitro and propagated as continuous lymphoblastoid cell lines for several years (IB4) or for less than 1 year (W91-LCL) (FIG. 3). EBI 1 RNA is faintly detectable in the human T cell line Jurkat, and is abundantly expressed in a second T cell line, HSB-2 (FIG. 3). EBI 2 RNA is not detected in either T cell line (FIG. 3), nor in a third T cell line, MOLT-4. EBI 1 is not expressed in the human promyelocytic line, HL60, the chronic myelogeneous leukemia cell line K562, the epithelial cell line, RHEK-1, the fibroblast-like osteosarcoma cell line, TK143, or the monocytic cell line, U937 (FIG. 3). EBI 2, however, is expressed weakly, relative to actin, in HL60, U937 (U937 RNA is partially degraded) or HeLa cells (FIG. 3).

EBI 1 and 2 RNAs are abundant in human spleen, somewhat less abundant relative to actin in tonsil and are not detectable in bone marrow (FIG. 3). Both genes were expressed in resting PBMCs at levels comparable to IB4 or LCL-W91 . B lymphoblastoid cells (FIG. 3). Expression increased in parallel cultures stimulated for 72 h with pokeweed mitogen (PWM), although actin expression also increased with PWM (FIG. 3). The EBI 1 and 2 RNA in stimulated and non stimulated PBMC cultures is likely to be mostly in B lymphocytes since EBI 1 RNA is at low levels and EBI 2 RNA is absent from phytohemagglutinin stimulated, PBMC derived, T lymphocytes (FIG. 3). These findings are consistent with expression patterns observed in T cell lines.

Figure 4:
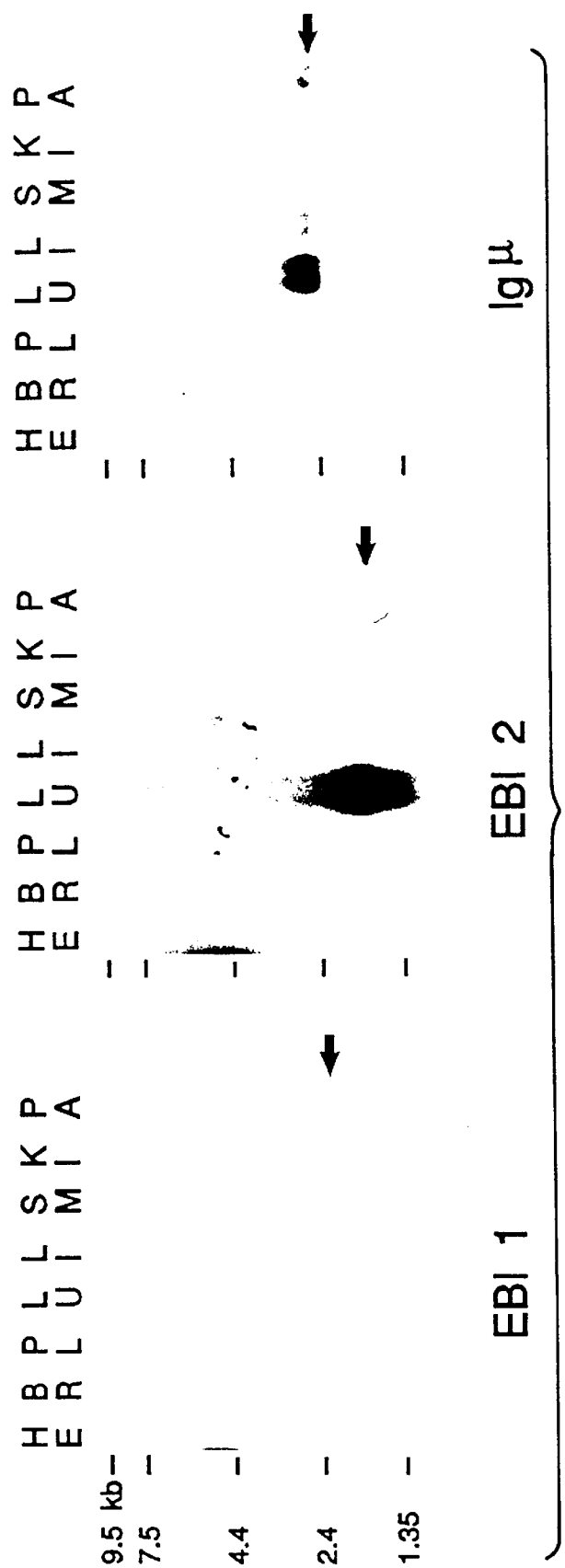

EBI 1 and 2 RNA levels were also evaluated in a variety of non-hematopoietic human tissues. The EBI 1 probe detects small amounts of RNA in both lung and pancreas (FIG. 4). Rehybridization of this blot with an immunoglobulin mu chain probe (FIG. 4, Igu probe) indicated that these tissue preparations contained significant amounts of immunoglobulin RNA, probably due to B lymphocytes in the tissues. Since EBI 1 RNA is abundant in peripheral blood lymphocytes, the EBI 1 RNA in the lung and pancreas is likely to be due to B lymphocytes. Similarly, the low level of EBI 2 RNA detected in pancreatic tissue is probably due to infiltrating B lymphocytes (FIG. 4). However, the abundance of EBI 2 RNA in the lung is too great to attribute to lymphocyte contamination and is more likely due to specific expression in pulmonary epithelial cells or macrophages (FIG. 4).

EXAMPLE 6

Cloning and Characterization of EBI 3

Subtractive hybridization screening of a BL41 /B95-8 cDNA library has permitted the identification of a number of genes expressed at higher levels in EVB-infected BL cells compared with matched EBV(−) cells. Twenty-five putative EBV-induced gene clones were initially isolated. Of these, 13 clones matched 8 previously known genes. The remaining 12 clones represented 10 novel genes. Two of these clones were derived from transcripts of a previously uncharacterized gene designated EBV-induced gene 3 (EBI 3).

The complete nucleotide and amino acid sequence of the larger EBI 3 clone are shown in FIG. 5 (SEQ ID NO:5 and SEQ ID NO:6, respectively). The 1182 nucleotide cDNA contains a 690 nucleotide open reading frame. A unique AUG codon preceding this reading frame at nucleotides 14–16 conforms to the Kozak consensus translational initiation sequence. Initiation from this site results in the synthesis of a polypeptide with a predicted molecular mass of 25,380 Daltons. The first 20 amino acids are highly hydrophobic and likely form a signal peptide for membrane translocation with a predicted signal peptidase cleavage site following a glycine residue at position 20. Two potential asparagine-linked glycosylation sites are also identified. However, no other hydrophobic segments capable of forming the transmembrane domain of an integral membrane protein are evident. To verify the structure of this cDNA, five additional clones were retrieved from the library. All of these exhibited identical sequences throughout the putative carboxy-terminal portion of the predicted protein. The 3' end of the EBI 3 nucleotide sequence is notable for its homology to the left monomer of the human Alu repeat element. This homology extends to and includes the A-rich sequences which immediately precede the polyadenylate tail of the mRNA.

The EBI 3 nucleotide and amino acid sequences were compared with all known sequences of Genbank nucleic acid, and Genbank translation, Protein Identification Resource (PIR) and Swiss Protein databases, respectively, using the Experimental GENINFO(R) BLAST-server network of the National Center for Biotechnology Information. No significant nucleotide homologies were observed, excluding matches with the 3' untranslated Alu repeat. However, the predicted EBI 3 protein is approximately 30% identical to the receptor for ciliary neurotrophic factor (CNTF), with conservative amino acid changes at many of the non-identical residues. Of particular significance is the pattern of conserved residues which include 4 cysteines at positions 35, 46, 80 and 90 respectively of the complete EBI 3 protein sequence; tryptophanes at positions 48 and 150; proline at position 125; and aliphatic hydrophobic residues at positions 128, 136, 148 and 204. In addition, the EBI 3 sequence LSDWS at residues 215 to 219 closely matches the WSDWS sequence of the CNTF receptor. These conserved structural features are characteristic of and unique to members of the cytokine receptor family. The predicted EBI 3 protein exhibits less extensive homologies with the p40 subunit of interleukin 12 (IL-12), also known as natural killer cell stimulatory factor. Though a secreted protein, IL-12 p40 possesses the same conserved residues and is also a member of the cytokine receptor family. In addition, the carboxy terminal 100 amino acids of the EBI 3 protein exhibit structural homologies with type III fibronectin domains of a variety of adhesion related molecules, including tenascin, cytotactin and the neural cell adhesion molecule, NCAM. This feature has also been described among other cytokine receptor family members.

Figure 6:
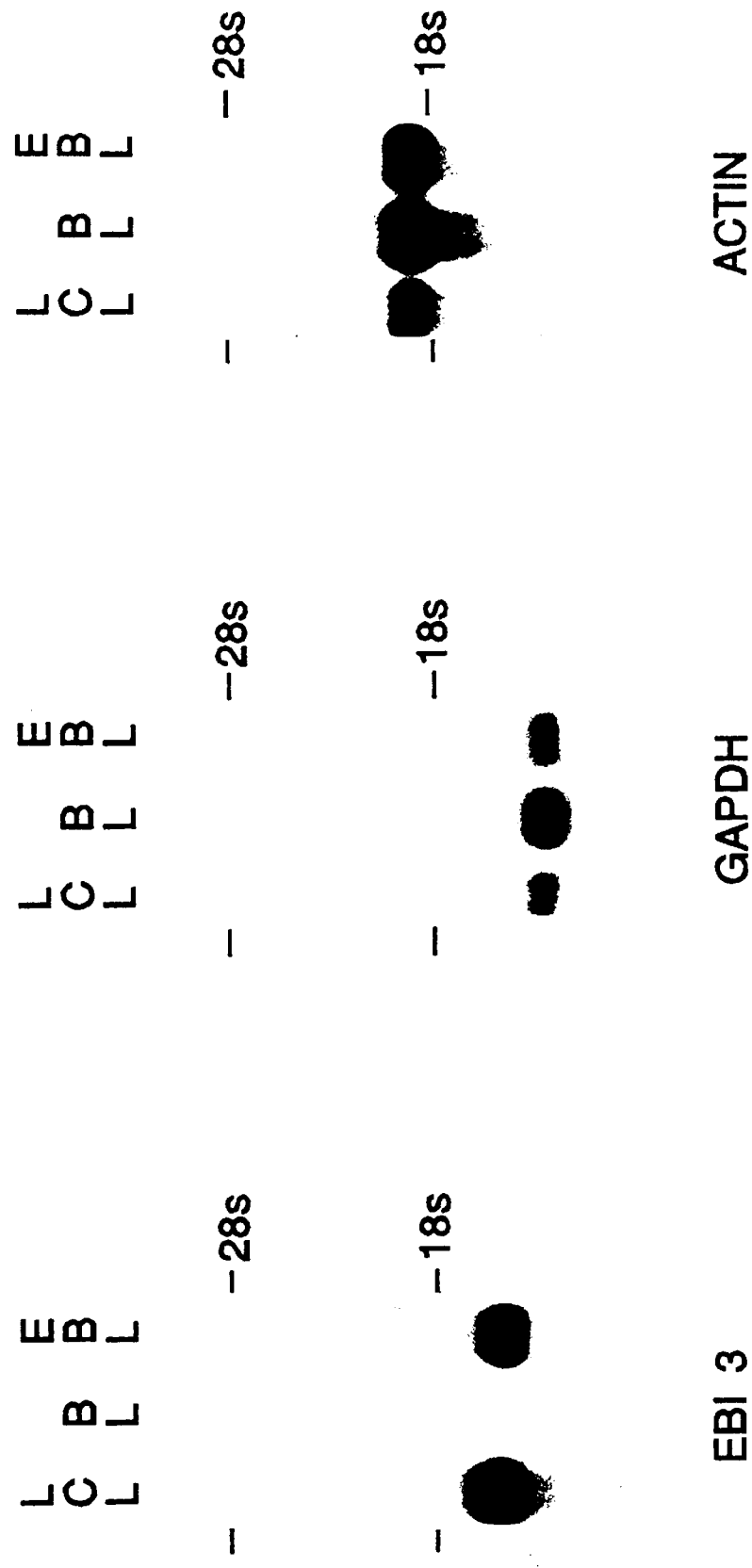
FIG. 6. RNA blot hybridization analysis of EBI 3 gene expression. Polyadenylated RNA (4 to 12 µg/lane) was size fractionated on formaldehyde agarose gel, transferred to an activated nylon membrane and hybridized with a 32P-labeled EBI 3 cDNA, actin and glyceraldehyde dehydrogenase (GAPDH) probes. RNA samples used in each lane are indicated at the top. (LCL is the EBV-immortalized primary B lymphoblastoid cell line, IB4; BL is the EBV-negative Burkitt lymphoma cell line, BL41; EBL is the EBV-infected Burkitt lymphoma cell line, BL41/B95-8, derived by in vitro infection of BL41 line.) An abundant 1.5 kb RNA is recognized by the EBI 3 probe in both EBV-infected cell line RNA samples (LCL, EBL), but is undetectable in the EBV-negative cell sample (BL). Control hybridization with actin and GAPDH probes indicate that the BL lane contains as much or more RNA than the EBV-infected cell lanes. Dashes indicate positions of ribosomal RNA bands (18s, 28s).

Hybridization of a $^{32}$P-labeled EBI 3 probe to RNA blots detects a 1.5 kb RNA in the EBV-infected cell lines IB4 and BL41/B95-8 (FIG. 6). EBI 3 RNA is undetectable, however, in the EVB(−) control cell line BL41. To provide standards for the amounts of RNA loaded in each line, parallel blots were hybridized with probes for glyceraldehyde phosphate dehydrogenase (GAPDH) and actin. These probes indicate that the BL41 lane contains as much or more RNA than the EBV-infected cell lanes.

Examination of a series of human cell lines and lymphoid tissues indicated that EBI 3 is expressed at very low levels in normal unfractionated resting lymphocytes of spleen and tonsil, but is undetectable in peripheral blood mononuclear cells (PBMC). However, stimulation of PBMC with the B and T lymphocyte activating agent, pokeweed mitogen, results in induction of the EBI 3 mRNA. Lower levels of EBI 3 RNA were detected in phytohemagglutinin stimulated peripheral blood T lymphocytes. In addition to IB4 and BL41/B95-8 cells, a recently established lymphoblastoid cell line transformed with the W91 EBV strain also exhibited significant EBI 3 expression. EBI 3 RNA was undetectable in a second EBV(−) BL cell line, BL30, in BL41 cells infected with the non-transforming P3HR1 EBV strain, and in all human myeloid, T lymphoid or epithelial cell line examined.

Figure 7A:
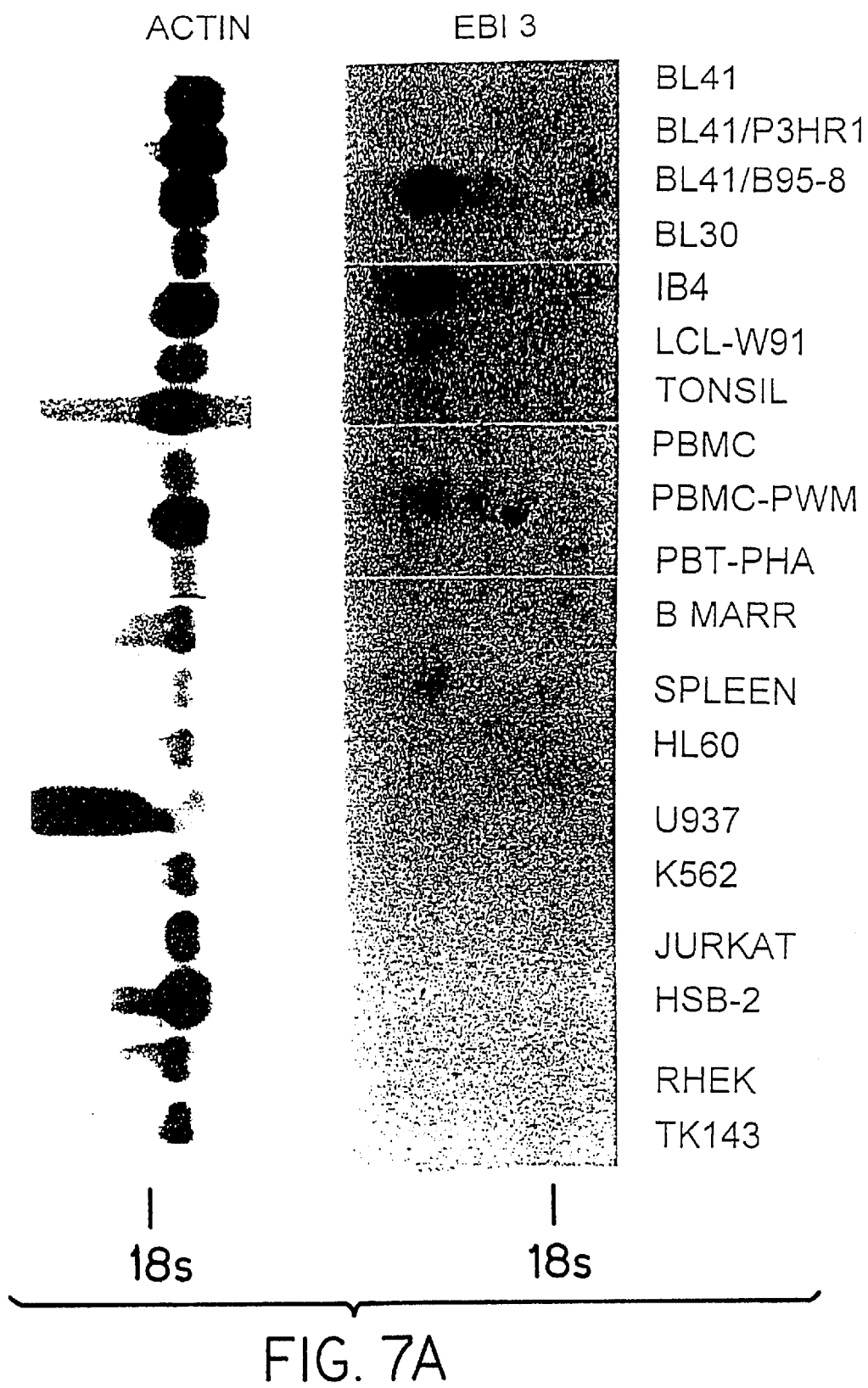
FIGS. 7A–B. Expression of EBI 3 gene RNA in human tissues and cell lines.
Figure 7B:
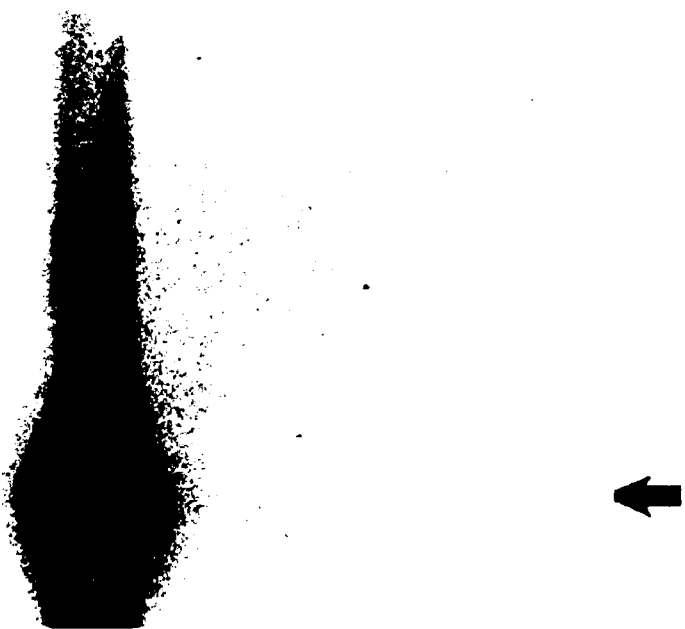

Expression of EBI 3 RNA was also analyzed in a variety of non-lymphoid human tissues (FIG. 7A). Abundant expression was observed in placenta, significantly exceeding expression levels observed in any lymphoid cell type. EBI 3 RNA was also faintly detectable in liver RNA. However, rehybridization of this blot with an immunoglobulin $\mu$ heavy chain probe indicated detectable Ig gene expression, probably due to infiltration of liver tissue with lymphocytes in vivo. The apparent expression of EBI 3 in liver could therefore be due to expression in resident lymphocytes.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

TABLE 1

Summary of EBV Induced RNA:cDNA Clones

| Clone | Gene | cDNA Size (kb) | RNA Size (kb) | Induction[1] |
|---|---|---|---|---|
| 1.1 | CD44 | 1,3 | 1.6, 2.2, 5.0 | >100X |
| 3.3; 7.3 | CD21 | 2.1; 1.8 | 4.8 | |
| 6.5 | MARCKS | 2.6 | 2.9 | 30X |
| 8.2 | Cathepsin H | 1.5 | 1.7 | 6X |
| 10.4; 11.4 | Serglycin | 1.1; 1.1 | 1.4 | 3.5X |
| 12.3 | Annexin VI | 2.3 | 3.0 | 5X |
| 12.5; 13.0 | Vimentin | 1.0; 1.8 | 2.0 | |
| 6.4 | EBI 1 | 1.2 (2.14)[2] | 2.4 | 21X |
| 3.2 | EBI 2 | 1.64 | 1.9 | >200X |
| | Beta actin | | 2.2 | 3X[3] |

[1]Induction levels were calculated as ratio of signal intensities (BL41/B95-8 to BL41) for individual probes, divided by ratio of signal intensities for Actin probe.
[2]The 1.2 kb EBI 1 clone identified on initial screen was incomplete. Rescreening of the cDNA library resulted in isolation of several additional full-length clones, the largest of which was 2.14 kb.
[3]Induction of beta actin RNA was calculated as ratio of actin signal intensities, to ratio of signal intensities for glyceraldehyde phosphate dehydrogenase probe.

What is claimed is:

1. An isolated polypeptide comprising the amino acid sequence of SEQ ID NO:2.

2. A fusion protein comprising the isolated polypeptide of claim 1 and one or more heterologous protein sequences fused thereto.

3. An isolated polypeptide comprising the amino acid sequence of SEQ ID NO:4.

4. A fusion protein comprising the isolated polypeptide of claim 3 and one or more heterologous protein sequences fused thereto.

5. An isolated polypeptide comprising the amino acid sequence of SEQ ID NO:6.

6. A fusion protein comprising the isolated polypeptide of claim 5 and one or more heterologous protein sequences fused thereto.

7. An isolated polypeptide consisting of a fragment of SEQ ID NO:2, wherein the fragment consists of at least 10 contiguous amino acids of the amino acid sequence of SEQ ID NO:2.

8. The isolated polypeptide of claim 7, wherein the fragment consists of at least 15 contiguous amino acids of the amino acid sequence of SEQ ID NO:2.

9. The isolated polypeptide of claim 7, wherein the fragment consists of at least 20 contiguous amino acids of the amino acid sequence of SEQ ID NO:2.

10. The isolated polypeptide of claim 7, wherein the fragment consists of at least 30 contiguous amino acids of the amino acid sequence of SEQ ID NO:2.

11. A fusion protein consisting of the isolated polypeptide of claim 7 and one or more heterologous protein sequences fused thereto.

12. An isolated polypeptide consisting of a fragment of SEQ ID NO:4, wherein the fragment consists of at least 10 contiguous amino acids of the amino acid sequence of SEQ ID NO:4.

13. The isolated polypeptide of claim 12, wherein the fragment consists of at least 15 contiguous amino acids of the amino acid sequence of SEQ ID NO;4.

14. The isolated polypeptide of claim 12, wherein the fragment consists of at least 20 contiguous amino acids of the amino acid sequence of SEQ ID NO:4.

15. The isolated polypeptide of claim 12, wherein the fragment consists of at least 30 contiguous amino acids of the amino acid sequence of SEQ ID NO:4.

16. A fusion protein consisting of the isolated polypeptide of claim 12 and one or more heterologous protein sequences used thereto.

17. An isolated polypeptide consisting of a fragment of SEQ ID NO:6, wherein the fragment consists of at least 10 contiguous amino acids of the amino acid sequence of SEQ ID NO:6.

18. The isolated polypeptide of claim 17, wherein the fragment consists of at least 15 contiguous amino acids of the amino acid sequence of SEQ ID NO:6.

19. The isolated polypeptide of claim 17, wherein the fragrant consists of at least 20 contiguous amino acids of the amino acid sequence of SEQ ID NO 6.

20. The isolated polypeptide of claim 17, wherein the fragment consists of at least 30 contiguous amino acids of the amino acid sequence of SEQ ID NO:6.

21. A fusion protein consisting of the isolated polypeptide of claim 17 and one or more heterologous protein sequences fused thereto.

22. An isolated EDI2 or EBI3 polypeptide encoded by an isolated nucleic acid molecule selected from the group consisting of
   (a) nucleic acid molecules consisting of nucleotide sequences set forth as SEQ ID NO:3 or SEQ ID NO.5, and
   (b) nucleic acid molecules which hybridize under stringent conditions to the nucleic acid molecules of (a) or a complement thereof, wherein stringent conditions are hybridization for 18 to 24 h at 47° C. in a hybridization buffer consisting of 50% formamide. 6×SSPE (20× SSPE: 3.0 M NaCl, 200 mM NaP04, pH7.4, 20 mM EDTA), 1% SDS, 1×Denhardt's solution (100× Denhardt's, 2% BSA, 2% polyvinylpyrrolidone, 2% Ficoll), and 100 µg/ml sheared single-stranded herring testis DNA and washing at 67° C.–70° C. in 1% SDS, 0.2×SCC.

23. The isolated polypeptide of claim 22, wherein the polypeptide Is encoded by an isolated nucleic acid molecule consisting of the nucleotide sequence of SEQ ID NO:3, or at least 20 contiguous nucleotides thereof.

24. The isolated polypeptide of claim 23, wherein the isolated nucleic acid molecule consists of at least 30 contiguous nucleotides of SEQ ID NO:3.

25. The isolated polypeptide of claim 23, wherein the isolated nucleic acid molecule consists of at least 50 contiguous nucleotides of SEQ ID NO:3.

26. The isolated polypeptide of claim 22, wherein the polypeptide is encoded by an isolated nucleic acid molecule consisting of the nucleotide sequence of SEQ ID NO:5, or at least 20 contiguous nucleotides thereof.

27. The isolated polypeptide of claim 26, wherein the isolated nucleic acid molecule consists of at least 30 contiguous nucleotides of SEQ ID NO:5.

28. The isolated polypeptide of claim 26, wherein the isolated nucleic acid molecule consists of at least 50 contiguous nucleotides of SEQ ID NO:5.

29. An isolated EBI1 polypeptide encoded by an isolated nucleic acid molecule selected from the group consisting of
   (a) a nucleic acid molecule consisting of a nucleotide sequence set forth as SEQ ID NO: 1, and
   (b) nucleic acid molecules which hybridize under stringent conditions to the nucleic acid molecules of (a) or a complement thereof, wherein the nucleic acid molecules which hybridize under stringent conditions comprise at least 30 contiguous nucleotides of SEQ ID NO.1,
   wherein stringent conditions are hybridization for 18 to 24 h at 47° C. in a hybridization buffer consisting of 50% formamide, 6×SSPE (20×SSPE: 3.0 M NaCl, 200 mM NaPO4, pH7.4, 20 mM EDTA), 1% SDS, 1×Denhardt's solution (100×Denhardt's: 2% BSA, 2% polyvinylpyrrolidone, 2% Ficoll), and 100 µg/ml sheared single-stranded herring testis DNA and washing at 67° C.–70° C. in 1% SDS, 0.2×SCC.

30. The isolated polypeptide of claim 29, wherein the isolated nucleic acid molecule comprises at least 50 contiguous nucleotides of SEQ ID NO: 1.

\* \* \* \* \*